(12) United States Patent
Breakefield et al.

(10) Patent No.: US 6,610,287 B1
(45) Date of Patent: Aug. 26, 2003

(54) TRANSFER AND EXPRESSION OF GENE SEQUENCES INTO NERVOUS SYSTEM CELLS USING HERPES SIMPLEX VIRUS MUTANTS WITH DELETIONS IN GENES FOR VIRAL REPLICATION

(75) Inventors: Xandra O. Breakefield, Newton, MA (US); Robert L. Martuza, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 08/363,998

(22) Filed: Dec. 27, 1994

Related U.S. Application Data

(63) Continuation of application No. 07/956,949, filed on Oct. 6, 1992, now abandoned, which is a continuation-in-part of application No. 07/745,824, filed on Aug. 16, 1991, now abandoned, which is a continuation-in-part of application No. 07/508,731, filed on Apr. 16, 1990, now abandoned.

(51) Int. Cl.[7] .................. A01N 63/00; A61K 48/00; A61K 31/70

(52) U.S. Cl. .................. 424/93.2; 424/93.6; 514/44

(58) Field of Search .................. 514/44; 424/93.2, 424/93.6

(56) References Cited

U.S. PATENT DOCUMENTS

| 4,686,186 A | 8/1987 | Sugden et al. .............. 435/243 |
| 5,501,979 A | 3/1996 | Geller et al. ............. 435/320.1 |
| 5,672,344 A | * 9/1997 | Kelley et al. |

FOREIGN PATENT DOCUMENTS

| EP | 0 453 242 | 10/1991 |
| EP | 0 487 611 | 6/1992 |
| WO | WO 90/02551 | 3/1990 |
| WO | WO 90/09441 | 8/1990 |

OTHER PUBLICATIONS

Breakefield et al Moleculr Neurology 1: 339, 1987.*
Cai et al Journal of Virology 63(11): 4579, 1989.*
Ho et al Virology 167: 279, 1988.*
Palella et al Gene 80: 137, 1989.*
Ho et al of record.
Cai et al of record.
Breakefield et al of record.
Tenser (1983) J. Infect. Diseases 147, 956.*
Holloway (Jan. 1991) Scientific American, 32.*
Sakimura et al (1987) Gene 60, 103–113.*
Geller et al (1988) Science 241, 1667–1669.*
Friedmann (1989) Science 244, 1275–1281.*
Breakefield et al (1991) The New Biol. 3, 203–218.*
Ho et al (1988) Virol. 167, 279–283.*

Arvidson, B., "Retrograde Transport of Horseradish Peroxidase In Sensory and Adrenergic Neurons Following Injection into the Anterior Eye Chamber," *Journal of Neurocytology* 8:751–764 (1979).
Baccaglini et al., "Some Rat Sensory Neurons In Culture Express Characteristics of Differentiated Pain Sensory Cells," *PNAS USA* 80:594–598 (1983).
Baetge et al., "Transgenic Mice Express the Human Phenylethanolamine N–Methyltransferase Gene In Adrenal Medulla and Retina," *PNAS USA* 85:3648–3652 (1988).
Bigotte et al., "Degeneration of Trigeminal Ganglion Neurons Caused by Retrograde Axonal Transport of Doxorubicin," *Neurology* 37:985–992 (1987).
Black et al., "Biochemistry of Information Storage In the Nervous System," *Science* 236:1263–1268 (1987).
Böhnlein et al., "Functional Analysis of the Regulatory Region of Polyoma Mutant F9–1 DNA," *Nuc. Acids Res.* 13(13): 4789–4809 (1985).
Breakefield et al., "Gene Transfer into the Nervous System," *Mol. Neurobiol.* 1:339–371 (1987).
Breakefield et al., "Herpes Simplex Virus for Gene Delivery to Neurons," *The New Biologist* 3(3) :203–218 (1991).
Cai et al., "Herpes Simplex Virus Type 1 ICP0 Plays a Critical Role In the De Novo Synthesis of Infections Virus Following Transfection of Viral DNA," *J. Virol.* 63(11) : 4579–4589 (1989).
Chiocca et al., "Transfer and Expression of the lacZ Gene In Rat Brain Neurons Mediated by Herpes Simplex Virus Mutants," *The New Biologist* 2(8):739–746 (1990).
Coen et al., "Thymidine Kinase–Negative Herpes Simplex Virus Mutants Establish Latency In Mouse Trigeminal Ganglia But Do Not Reactivate," *PNAS USA* 86:4736–4740 (1989).
Colbere–Garapin et al., "Cloning of the Active Thymidine Kinase Gene of Herpes Simplex Virus Type 1 in *Escherichia coli* K–12," *PNAS USA* 76(8):3755–3759 (1979).
Croen et al., "Latent Herpes Simplex Virus In Human Trigeminal Ganglia," *The New England J. of Med.* 317(23):1427–1432 (1987).
Cook et al., "Pathogenesis of Herpetic Neuritis and Ganglionitis In Mice: Evidence for Intra–Axonal Transport of Infection," *Infect. and Immun.* 7(2):272–288 (1973).
Davison et al., "Determination of the Sequence Alteration In the DNA of the Herpes Simplex Virus Type 1 Temperature–sensitive Mutant ts K," *J. Gen Virol.* 65:859–863 (1984).

(List continued on next page.)

Primary Examiner—Deborah Crouch
(74) Attorney, Agent, or Firm—Sterne, Kessler, Goldstein & Fox, P.L.L.C.

(57) ABSTRACT

This invention relates to methods of gene delivery to cells in the nervous system by introducing and expressing gene sequences mediated by herpes simplex virus 1 (HSV-1) vectors with a mutation in a gene for viral replication. The present invention further relates to methods for modulating neuronal physiology and for treating nervous system disorders. The present invention also relates to an animal model for nervous system disorders and to methods for producing such an animal model.

12 Claims, 14 Drawing Sheets

OTHER PUBLICATIONS

De Koninc et al., "Substance P–Mediated Slow Excitatory Postsynaptic Potential Elicited In Dorsal Horn Neurons In Vivo by Noxious Stimulation," *PNAS USA* 88:11344–11348 (1991).

Dobson et al., "A Latent Nonpathogenic HSV–1–Derived Vector Stably Expresses β–Galactosidase In Mouse Neurons," *Neuron* 5:353–360 (1990).

Dobson et al., "Identification of the Latency–Associated Promoter by Expression of Rabbit Beta–Globin mRNA In Mouse Sensory Nerve Ganglia Latently Infected with a Recombinant Herpes Simplex Virus," *J. of Virology* 63(9):3844–3851 (1989).

Efstathiou et al., "The Role of Herpes Simplex Virus Type 1 Thymidine Kinase In Pathogenesis," *J. Gen. Virol.* 70:869–879 (1989).

Efstathiou et al., "Detection of Herpes Simplex Virus–Specific DNA Sequences In Latently Infected Mice and In Humans," *J. of Virology* 57(2):446–455 (1986).

Fenwick, M.L., "The Effects of Herpesviruses On Cellular Macromolecular Synthesis," *Compr. Virol.* 19:359–390 (1984).

Forss–Petter et al., "Transgenic Mice Expressing β–Galactosidase In Mature Neurons Under Neuron–Specific Enolase Promoter Control," *Neuron* 5:187–197 (1990).

Friedmann, T., "Progress Toward Human Gene Therapy", *Science* 244:1275–1281 (1989).

Geller et al., "Infection of Cultured Central Nervous System Neurous with a Defective Herpes Simplex Virus 1 Vector Results In Stable Expression of *Escherichia coli* β–Galactosidase," *PNAS USA* 87:1149–1153 (1990).

Geller et al., "A Defective HSV–1 Vector Expresses *Escherichia coli* β–Galactosidase In Cultured Peripheral Neurons," *Science* 241:1667–1669 (1988).

Heilbronn et al., "A Subset of Herpes Simplex Virus Replication Genes Induces DNA Amplification within the Host Cell Genome," *J. of Virology* 63 (9) :3683–3692 (1989).

Ho et al., "β–Galactosidase as a Marker In the Peripheral and Neural Tissues of the Herpes Simplex Virus–Infected Mouse," *Virology* 167:279–283 (1988).

Ho et al., "Herpes Simplex Virus Latent RNA (LAT) Is Not Required for Latent Infection In the Mouse," *PNAS USA* 86:7596–7600 (1989).

Huang et al., "Introduction of a Foreign Gene (*Escherichia coli* lacZ) into Rat Neostriatal Neurons Using Herpes Simplex Virus Mutants: A Light and Electron Microscopic Study," *Experimental Neurology* 115:303–316 (1992).

Javier et al., "Localization of a herpes Simplex Virus Neurovirulence Gene Dissociated from High–Titer Virus Replication In the Brain," *J. of Virology* 62 (4) :1381–1387 (1988).

Javier et al., "A Herpes Simplex Virus Transcript Abundant In Latently Infected Neurons Is Dispensable for Establishment of the Latent State," *Virology* 166:254–257 (1988).

Koprowski, H., "Possible Role of Herpes Virus In the Chronic CNS Diseases", in *Persistent Viruses*, F.G. Stevens (ed.), Academic Press, N.Y., pp. 691–699 (1978).

Kosz–Vnenchak et al., "Restricted Expression of Herpes Simplex Virus Lytic Genes During Establishment of Latent Infection by Thymidine Kinase–Negative Mutant Viruses", *J. of Virology* 64 (11):5396–5402 (1990).

Kuwayama et al., "A Quantitative Correlation of Substance P–, Calcitonin Gene–Related Peptide– and Cholecystokinin–LIke Immunoreactivity with Retrogradely Labeled Trigeminal Ganglion Cells Innervating the Eye," *Brain Research* 405:220–226 (1987).

Kuypers et al., "Viruses as Transneuronal Tracers," *TINS* 13(2):71–75 (1990).

Kwong et al., "The Herpes Simplex Virus Virion Host Shutoff Function," *J. of Virology* 63(11) :4834–4839 (1989).

Leib et al., "A Deletion Mutant of the Latency–Associated Transcript of Herpes Simplex Virus Type 1 Reactivates from the Latent State with Reduced Frequency," *J. of Virology* 63 (7):2893–2900 (1989).

Leib et al., "Immediate–Early Regulatory Gene Mutants Define Different Stages In the Establishment and Reactivation of Herpes Simplex Virus Latency," *J. of Virology* 63(2):759–768 (1989).

Leist et al., "Latent Infections In Spinal Ganglia with Thymidine Kinase–Deficient Herpes Simplex Virus", *J. of Virology* 63(11) :4976–4978 (1989).

Longnecker et al., "Herpes Simplex Viruses as Vectors: Properties of a Prototype Vaccine Strain Suitable for Use as a Vector", in *Viral Vectors*, Gluzman et al. (eds.), CSH Lab, pp. 68–72 (1988).

Marangos et al., "Neuron Specific Enolase, a Clinically Useful Marker for Neurons and Neuroendocrine Cells," *Ann. Rev. Neuroscience* 10: 269–295 (1987).

Margolis et al., "Identifying HSV Infected Neurons After Ocular Inoculation," *Current Eye Research* 6(1) :119–126 (1987).

Margolis et al., "Pathways of Viral Gene Expression during Acute Neuronal Infection with HSV–1," *Virology* 189:150–160 (1992).

Margolis et al., "Selective Spread of Herpes Simplex Virus In the Central Nervous System After Ocular Innoculation," *J. of Virology* 63(11):4756–4761 (1989).

Martuza et al., "Experimental Therapy of Human Glioma by Means of a Genetically Engineered Virus Mutant," *Science* 252:854–856 (1991).

Mellerick et al., "Physical State of the Latent Herpes Simplex Virus Genome In a Mouse Model System: Evidence Suggesting an Episomal State," *Virology* 158:265–275 (1987).

Miura et al., "Cell–Specific Expression of the Mouse Glial Fibrillary Acidic Protein Gene: Identification of the Cis– and Trans–Acting Promoter Elements for Astrocyte–Specific Expression," *J. of Neurochem.* 55:1180–1188 (1990).

Norgren et al., "Retrograde Transneuronal Transport of Herpes Simplex Virus In the Retina After Injection In the Superior Colliculus, Hypothalamus and Optic Chiasm," *Brain Research* 479:374–378 (1989).

Oberdick et al., "A Promoter That Drives Transgene Expression In Cerebellar Purkinje and Retinal Bipolar Neurons," *Science* 248:223–226 (1990).

Palella et al., "Expression of Human HPRT mRNA In Brains of Mice Infected with a Recombinant Herpes Simplex Virus–1 Vector," *Gene* 80:137–144 (1989).

Palmer et al., "Genetically Modified Skin Fibroblasts Persist Long After Transplantation But Gradually Inactivate Introduced Genes," *PNAS USA* 88:1330–1334 (1991).

Palmiter et al., "SV40 Enhancer and Large–T Antigen Are Instrumental In Development of Choroid Plexus Tumors In Transgenic Mice," *Nature* 316:457–460 (1985).

Price et al., "Lineage Analysis In the Vertebrate Nervous System by Retrovirus–Mediated Gene Transfer," *PNAS USA* 84:156–160 (1987).

Rock et al., "Detection of Latency–Related Viral RNAs In Trigeminal Ganglia of Rabbits Latently Infected with Herpes Simplex Virus Type 1," *J. of Virology* 61(12):3830–3826 (1987).

Rock et al., "Detection of HSV–1 Genome In Central Nervous System of Latently Infected Mice," *Nature* 302:523–525 (1983).

Roizman et al., "Herpesviruses and Their Replication", in *Virology*, B.N. Fields et al. (eds.), pp. 497–526, Raven Press, New York (1985).

Sacks et al., "Deletion Mutants In the Gene Encoding the Herpes Simplex Virus Type 1 Immediate–Early Protein ICP0 Exhibit Impaired Growth In Cell Culture," *J. Virology* 61(3):829–839 (1987).

Sanes et al., "Use of a Recombinant Retrovirus to Study Post–Implantation Cell Lineage In Mouse Embryos," *The EMBO Journal* 5(12):3133–3142 (1986).

Sawtell et al., "Herpes Simplex Virus Type 1 Latency–Associated Transcription Unit Promotes Anatomical Site–Dependent Establishment and Reactivation from Latency," *J. of Virology* 66(4):2157–2169 (1992).

Shepard et al., "Separation of Primary Structural Components Conferring Autoregulation, Transaction, and DNA–Binding Properties to the Herpes Simplex Virus Transcription Regulatory Protein ICP4," *J. of Virology* 63(9):3714–3728 (1989).

Smibert et al., "Differential Regulation of Endogenous and Transduced β–Globin Genes During Infection of Erythroid Cells with a Herpes Simplex Virus Type 1 Recombinant," *J. of Virology* 64(8):3882–3894 (1990).

Smiley et al., "Expression of a Cellular Gene Cloned In Herpes Simplex Virus: Rabbit Beta–Globin Is Regulated as an Early Viral Gene In Infected Fibroblasts," *J. of Virology* 61(8):2368–2377 (1987).

Smiley, J.R., "Construction In Vitro and Rescue of a Thymidine–Deficient Deletion Mutation of Herpes Simplex Virus," *Nature* 285:333–335 (1980).

Spaete et al., "The Herpes Simplex Virus Amplicon: A New Eucaryotic Defective–Virus Cloning–Amplifying Vector," *Cell* 30:295–304 (1982).

Spaete et al., "The Herpes Simplex Virus Amplicon: Analyses of Cis–Acting Replication Functions," *PNAS USA* 82:694–698 (1985).

Spivack, et al., "Detection of Herpes Simplex Virus Type 1 Transcripts During Latent Infection In Mice," *J. of Virology* 61(12):3841–3847 (1987).

Stevens, J.G., "Latent Characteristics of Selected Herpesviruses," *Adv. Cancer Research* 26:227–256 (1978).

Stevens, J.G., "Latent Herpes Simplex Virus and the Nervous System," *Curr. Top. Microbiol. Immunol.* 70:31–50 (1975).

Stevens, J.G., "Human Herpesviruses: A Consideration of the Latent State," *Microbiological Reviews* 53(3) : 318–332 (1989).

Stevens et al., "RNA Complementary to a Herpesvirus α Gene mRNA Is Prominent In Latently Infected Neurons," *Science* 235:1056–1059 (1987).

Ugolini et al., "Transneuronal Transfer of Herpes Virus from Peripheral Nerves to Cortex and Brainstem," *Science* 243:89–91 (1989).

Boothman et al., "Expression of the *E. coli* Lac Z Gene from a Defective HSV–1 Vector in Various Human Normal, Cancer–Prone and Tumor Cells", *FEBS* 258(1):159–162 (Nov. 1989).

DeLuca et al., "Physical and Functional Domains of the Herpes SimplexVirus Transcriptional Regulatory Protein ICP4," *J. Virol.* 62:732–743 (1988).

Denniston et al., "Characterization of Coliphage Lambda Hybrids Carrying DNA Fragments from Herpes simplex Virus Type 1 Defective Interfering Particles", *Gene* 15:365–378 (1981).

During et al., "Neuronal Expression of Parvalbumin and Calcium/Calmodulin Dependent Protein Kinase II from HSV–1 Vectors", *Abstr. Soc. Neurosci.* 16:501 [Abstr. No. 216.4] (Aug. 1990).

Enquist et al., "Cloning of Herpes Simplex Type 1 DNA Fragments in a Bacteriophage Lambda Vector", *Science* 203:541–544 (Feb. 9, 1979).

Federoff et al., "Neuronal Specific Expression of the Human Neurofilament L Promoter in a HSV–1 Vector", *Abstr. Soc. Neurosci.* 16:353 [Abstr. No. 154.2] (Aug. 1990).

Field et al., "The pathogenicity of thymidine kinase–deficient mutants of herpes simplex virus in mice," *J. Hyg. Camb.* 81:267–277 (1978).

Freese et al., "HSV–1 Vector Mediated Neuronal Gene Delivery", *Biochem. Pharm.* 40(10):2189–2199 (1990).

Frenkel et al., "Defective Virus Vectors (Amplicons) Derived from Herpes Simplex Viruses", *Gene Transfer and Cancer*, pp. 105–113, M.L. Pearson and N.L. Sternberg (eds.), Raven Press, NY (1984).

Frenkel et al., "The Herpes Simplex Virus Amplicon—A Novel Animal–virus Cloning Vector", *Eukaryotic Viral Vectors*, pp. 205–209, Cold Spring Harbor Laboratory Press, Cold Spring Harbor, NY (1982).

Geller, A.I., "A New Method to Propagate Defective HSV–1 Vectors", *Nucl. Acids Res.* 16(12):5690 (1988).

Geller, A.I., "A System, Using Neural Cell Lines to Characterize HSV–1 Vectors Containing Genes which Affect Neuronal Physiology, or Neuronal Promoters", *J. Neurosci. Meth.* 36:91–103 (1991).

Geller, A.I. "Influence of the Helper Virus on Expression of β–Galactosidase from a Defective HSV–1 Vector, pHSV-lac", *J. of Vir. Meth.* 31:229–238 (1991).

Geller et al., "An Efficient Deletion Mutant Packaging System for Defective Herpes Simplex Virus Vectors: Potential Applications to Human Gene Therapy and Neuronal Physiology", *PNAS USA* 87:8950–8954 (Nov. 1990).

Geller et al., "Expression of the Human Tyrosine Hydroxylase Gene in Cultured Fibroblasts and Striatal Neurons from a HSV–1 Vector: Possible Gene Therapy for Parkinson's Disease", *J. Cell Biol.* III(5) [Part 2]:339a [Abstr. No. 1899] (1990).

Geller et al., "Herpes Simplex Virus–1 (HSV–1) Vector System for Introduction of Foreign Genes to Rat Brain Neuron", *Chem. Abstr.* 112(5):128 [Abstr. No. 31241q] (Jan. 29, 1990).

Geller et al., "Transfection of Neurons with a Defective HSV–1 Vector and Expression of β–Galactosidase", *Abstr. Soc. Neurosci.* 14(Part I):624 [Abstr. No. 25411] (Aug. 1988).

Gerdes et al., "Acute Infection of Differentiated Neuroblastoma Cells by Latency–Positive and Latency–Negative Herpes Simplex Virus ts Mutants," *Virology* 94:430–441 (1979).

Holloway, M., "Neural Vector—Herpes May Open the Way to Gene Therapy in Neurons", Sci. Am. 264:32 (Jan. 1991).

Kwong et al., "Herpes Simplex Virus Amplicon: Effect of Size on Replication of Constructed Defective Genomes Containing Eucaryotic DNA Sequences", J. Virol. 51(3):595–603 (Sep. 1984).

Neve et al., "Fusion of the Aminoterminal 10 Amino Acids of GAP–43 to Beta–Galactosidase Targets the Chimeric Protein to Neuronal Processes", Abstr. Soc. Neurosci. 16:50 [Abstr. No. 27.6] (Aug. 1990).

Palella et al., "Herpes Simplex Virus–Mediated Human Hypoxanthine–Guanine Phopshoribosyltransferase Gene Transfer into Neuronal Cells," Mol. and Cell. Biol. 8(1):457–460 (Jan. 1988).

Paterson et al., "Mutational Dissection of the HSV–1 Immediate–Early Protein Vmw175 Involved in Transcriptional Transactivation and Repression", Virology 166:186–196 (1988).

Kwong et al., "The Herpes Simplex Virus Amplicon: Efficient Expression of a Chimeric Chicken Ovalbumin Gene Amplified within Defective Virus Genomes", Virology 142:421–425 (1985).

Marchioli et al., "Use of Recombinant Herpes Simplex Virus Type 1 as an Expression Vector to Induce Immunity to the Major Excreted Glycoprotein of Pseudorabies Virus," Abstracts of the Annual Meeting of the American Society for Microbiology:286, Abstract No. S 28 (1985).

Matz et al., "Physical Mapping of Temperature–sensitive Mutations of Herpes Simplex Virus Type 1 Using Cloned Restriction Endonuclease Fragments," J. Gen. Virol. 64:2261–2270 (1983).

Shih et al., "Herpes Simplex Virus as a Vector for Eukaryotic Viral Genes," in Lerner, R.A. et al., eds., Vaccines 85, Cold Spring Harbor Laboratory, pp. 177–180 (1985).

Suhar et al., "HSV Alpha Genes Are Preferentially Transcribed in a Transient Expression System," Abstracts of the Annual Meeting of the Amercian Society for Microbiology: 286, Abstract No. S 27 (1985).

Vlazny et al., "Replication of Herpes Simplex Virus DNA: Localizaiton of Replication Recognition Signals within Defective Virus Genomes", PNAS USA 78(2):742–746 (Feb. 1981).

Robbins et al., "Construction of E. coli Expression Plasmid Libraries: Localization of a Pseudorabies Virus Glycoprotein Gene," J. Mol. Appl. Genet. 2:485–496 ((1984).

Sakimura et al., "The structure and expression of neuron–specific enolase gene," Gene 60:103–113 (1987).

Shih et al., "Expression of Hepatitis B Virus S Gene by Herpes Simplex Virus Type 1 Vectors Carrying α– and β–Regulated Gene Chimeras", PNAS USA 81:5867–5870 (Sep. 1984).

Wagner et al., "Physical Characterisation of the Herpes Simplex Virus Latency–Associated Transcript in Neurons", J. of Virology 62(4):1194–1202 (1988).

Wigdahl et al., "Herpes Simplex Virus Latency In Isolated Human Neurons", PNAS USA 81 :6217–6221 (1984).

Watson et al., "Latency Competence of Thirteen HSV–1 Temperature–sensitive Mutants," J. Gen. Virol. 49:149–159 (1980).

Yan et al., "Restriction Mapping for the Thymidine Kinase Gene of Herpes Simplex Virus Type 1," Abstracts of the Annual Meeting of the Amerian Society for Microbiology:286, Abstract No. S 30 (1985).

Bear et al., "Analysis of Two Potential Shuttle Vectors Containing Herpes Simplex Virus Defective DNA," J. Mol. Appl. Genet. 2:471–484 (1984).

Clements, G.B., and Stow, N.D., "A Herpes Simplex Virus Type 1 Mutant Containing a Deletion within Immediate Early Gene 1 Is Latency–competent in Mice," J. gen. Virol. 70:2501–2506 9 (Sep. 1989).

DeLuca, N.A., et al., "Isolation and Characterization of Deletion Mutants of Herpes Simplex Virus Type 1 in the Gene Encoding Immediate–Early Regulatory Protein ICP4," J. Virol. 56(2):558–570 (1985).

Field, H.J., and Darby, G., "Pathogenicity in Mice of Strains of Herpes Simplex Virus Which Are Resistant to Acyclovir In Vitro and In Vivo," Antimicrob. Agents Chemother. 17(2):209–216 (1980).

Fink, D.J., et al., "Development of a Herpes Simplex Virus–mediated Gene Transfer Latency Vector," Annals of Neurology 28(2):220 (Aug. 1990).

Palella, T.D., et al., "Herpes Simplex Virus (HSV–1) Mediated Human Hypoxanthine–Guanine Phosphoribosyltranferase (HPRT) Gene Transfer into Neuronal Cells," Pediatric Research 24:129 (Abstract No. 107) (1988).

Post, L.E., et al., "Chicken Ovalbumin Gene Fused to a Herpes Simplex Virus α–Promoter and Linked to a Thymidine Kinase Gene Is Regulated Like a Viral Gene," Mol. Cell. Biol. 2(3):223–240 (1982).

"Strategies for Studying Gene Regulation," in: Molecular Cloning: A Laboratory Manual, Sambrook, J., Fritsch, E.F., and Maniatis, T., eds., Cold Spring Harbor Laboratory Press: Cold Spring Harbor, N.Y., pp. 16.56–16.58 (1989).

Stroop, W.G., et al., "Localization of Herpes Simplex Virus in the Trigeminal and Olfactory Systems of the Mouse Central Nervous System during Acute and Latent Infections by in Situ Hybridizaiton," Lab. Invest. 51(1):27–38 (1984).

Tenser, R.B., "Intracerebral Inoculation of Newborn and Adult Mice with Thymidine Kinase–Deficient Mutants of Herpes Simplex Virus Type 1," J. Infect. Dis. 147(5):956 (1983).

Tomlinson, A.H., and Esiri, M.M., "Herpes Simplex Encephalitis. Immunohistological Demonstration of Spread of Virus via Olfactory Pathways in Mice," J. Neurol. Sci. 60:473–484 (1983).

Fink, D.J., et al., "Gene Transfer into Brain Using a Herpes Simplex Virus (HSV) Vector," Soc. Neurosci. Abs. 16(Pt. 2):964 (Abstract No. 399.3) (Oct. 1990).

Lofgren, K.W., et al., "Temperature–Sensitive Mutants of Herpes Simplex Virus Differ in the Capacity To Establish Latent Infections in Mice," Virology 76:440–443 (1977).

Palella, T.D., et al., "Herpes Simplex Virus Mediated Human Hypoxanthine Phosphoribosyltransferase Gene Transfer Into Neuronal Cells," Clinical Research 35(3):650A (1987).

* cited by examiner

7134  RH105

*1 DAY*

*3 DAY*

*14 DAY*

TRANSFER AND EXPRESSION OF GENE SEQUENCES INTO NERVOUS SYSTEM CELLS USING HERPES SIMPLEX VIRUS MUTANTS WITH DELETIONS IN GENES FOR VIRAL REPLICATION

This application is a continuation, of application Ser. No. 07/956,949, filed Oct. 6. 1992, abandoned which is a continuation-in-part of application Ser. No. 07/745,824, filed on Aug. 16, 1991, abandoned, which is a continuation-in-part of application Ser. No. 07/508,731, filed Apr. 16. 1990, abandoned.

The present invention was made utilizing funds of the United States Government. The United States Government is hereby granted a worldwide royalty fee, paid up, non-exclusive license in the invention.

FIELD OF THE INVENTION

This invention relates to methods of gene delivery into cells of the nervous system, for example, cells of the central and peripheral nervous system, by introducing and expressing gene sequences using herpes simplex virus 1 (HSV-1) mutants with deletions in gene(s) for viral replication.

BACKGROUND OF THE INVENTION

The delivery and expression of heterologous or native genes into cells of the nervous system to alter normal cellular biochemical and physiologic processes in a stable and controllable manner is of substantial value in the fields of medical and biological research. This genetic perturbation of the nervous system provides a means for studying the molecular aspects of neuronal function and offering therapeutic approaches to pathologic processes.

Herpes simplex viruses possess several properties that render them attractive candidates as delivery vehicles to bring foreign genes into cells of the peripheral and central nervous systems. (Breakefield et al., *Mol. Neurobiol.* 1:339 (1987); Dobson et al., *J. Virol.* 63:3844–3851 (1989); Ho and Mocarski, *Virology* 167:279–283 (1988); Ho et al., *Proc. Natl. Acad. Sci. USA* 86:7596–7600 (1989); Breakefield and DeLuca, *New Biologist* 3:203–218 (1991); Chiocca et al., *New Biologist* 2:739–746 (1990); Friedmann, T., *Science* 244:1275–1280; Palella et al., *Gene* 80:138 (1989).)

These viruses can infect and deliver their DNA into many different cell types, including adult postmitotic neurons; they can enter a state of latency in neurons including, for example, sensory neurons, in which the viral genome exists as an episomal element in the nucleus of the cell; they are able to infect a substantial number of cells in vivo due to their ability to reach high titers in culture and to propagate in the nervous system and due to the relatively long half life of virus particles; large exogenous DNA sequences can be inserted into their genomes; and they possess a wide host range. (Longnecker et al., In: *Viral Vectors,* Gluzman et al. (eds.), CSH Lab, pp. 68–72 (1988); Roizmann et al., In: *Virology,* Fields et al. (eds.), Raven Press, New York, pp. 497–526 (1985); Rock et al., *Nature* 302:523–525 (1983).)

Recently, an amplicon-type plasmid-vector system based on herpes simplex virus 1 (HSV-1) has been used to achieve relatively stable expression of the lacZ gene in cultured neurons. (Spaete et al., *Proc. Natl. Acad. Sci. USA* 82:694 (1985); Geller et al., *Science* 241:1667 (1988); Geller et al., *Proc. Natl. Acad. Sci. USA* 87:1149 (1990).) In this plasmid vector, the lacZ gene was placed under the control of an HSV-1 immediate-early promoter and packaged using a temperature-sensitive HSV-1 helper virus tsK. Coen et al., *Proc. Natl. Acad. Sci. USA* 86:4736 (1989); Leib et al., *J. Virol.* 63:759 (1989); Davison et al., *J. Gen. Virol.* 65:859 (1984).)

Herpes simplex or other neurotropic viral vectors (Loewy et al., *Proc. Soc. Neurosci.* 17:603–15 (1991)) offer one potential means of delivering functional genes to alter the physiology of sensory or other neurons. Herpes simplex virus is known to be retrogradely transported from sensory terminals to sensory ganglia by a mechanism of fast axonal transport (Cook et al., *Infec. and Immun.* 7:272–288 (1973). HSV that reaches the nucleus of a sensory neuron, is capable of either lytic replication or latent infection. Lytic replication is characterized by the production of mature virus particles and destruction of the cell. Latent infection is characterized by the long-term stable presence of viral DNA in the nuclei of infected cells, most likely in the form of an episomal unit (Rock et al., *Nature* 302:523–525 (1983); Efstathiou et al., *J. Virol* 57(2):446–455 (1986); Mellerick et al., *Virol* 158:265–275 (1987)), and transcription that is limited to a specific region of the HSV genome (Croen et al., *New Engl. J. Med.* 317:1427–1432 (1987); Rock et al., *J. Virol.* 61:3820–3826 (1987); Spivak et al., *J. Virol.* 61:3841–3847 (1987); Stevens et al., *Science* 235:105–1059 (1987); Javier et al., *Virol.* 166:254–257 (1988); Wagner et al., *J. Virol.* 62(4):1194–1202 (1988); Kosz-Vnenchak et al., *J. Virol.* 64:5396–5402 (1990)).

Latent infection with HSV in the absence of lytic replication is possible using replication-defective recombinant vectors mutated by deletion, or insertion, of foreign elements into HSV genes necessary for replication (Dobson et al., *Neuron* 5:353–360 (1990); Andersen et al., *Human Gene Therapy* (in press) (1992)). Foreign genes stably expressed by these vectors have included lacZ (Ho and Mocarski '89) or rabbit β-globin inserted downstream of the putative HSV LAT promoter (Dobson et al., *J. Virol* 63:3844–3851 (1989)), and lacZ inserted downstream of the Moloney murine leukemia virus long terminal repeat (MoMLV-LTR) retrovirus promoter into the HSV immediate early gene ICP4 (vector 8117/43)(Dobson et al., *Neuron* 5:353–360 (1990)). Stable expression of foreign genes in the central and peripheral nervous system may also be possible using vectors that are replication-defective due to a mutation in the thymidine kinase (tk) gene. These thymidine kinase deficient (TK$^-$) mutants can replicate in the periphery in dividing cells, but are replication-defective in trigeminal ganglion neurons (Coen et al., *Proc. Natl. Acad. Sci. USA* 86:4736–4740 (1989); Efstathiou et al., *J. Gen. Virol.* 70:869–879 (1989)). TK$^-$ viruses may preferentially enter latency in sensory neurons (Kosz-Vnenchak et al., *J. Virol.* 64:5396–5402 (1990)), are unable to reactivate from latency to produce a lytic infection (Coen et al., *Proc. Natl. Acad. Sci. USA* 86:4736–4740 (1989); Efstathiou et al., *J. Gen. Virol.* 70:869–879 (1989)).

Several factors appear to limit the potential uses of herpes viruses for gene transfer to cells in culture and in vivo. These include the relatively frequent occurrence of spontaneous revertants of some mutants; possible recombination events between helper virus, viral sequences in plasmids, and latent sequences; deleterious effects on host cell macromolecular synthesis due to the presence of viral proteins; alterations in the host cell genome; and possible reactivation of preexisting latent viruses. (Davison et al., *J. Gen. Virol.* 65:859 (1984); Fenwick, M., *Compr. Virol.* 19:359 (1984); Heilbronn et al., *J. Virol.* 63:3683 (1989); Kwong et al., *J. Virol.* 63:4834 (1989); Johnson et al., *14th International Herpes Workshop* abst. (1989)).

In the study of gene expression in neuronal cells in the nervous system, and the identification of therapies for treating neuronal disease of the nervous system, a need therefore continues to exist for methods of gene delivery with efficient viral vectors capable of mediating gene transfer into such cells without causing harm to the host animal.

SUMMARY OF THE INVENTION

The present invention is directed to a method for introducing gene sequences into cells of the nervous system, for example, in the cells of the central and peripheral nervous system using HSV-1 mutants as vectors for gene delivery. The HSV-1 virus is mutated so that it has a deletion(s) in a gene(s) necessary for viral replication in neurons, for example in sensory ganglia in vivo. The desired gene sequence to be delivered to the cell is inserted into the mutated HSV-1 such that the gene sequence will be expressed in the host cell. By the method according to this invention, a gene sequence is expressed in a cell in the nervous system by introducing the mutated HSV-1 vector with a mutation in a gene necessary for viral replication in neurons and with a gene sequence located downstream of a promoter sequence so that the gene sequence will be expressed in the host cell.

The vectors of the present invention are capable of stable expression of the foreign gene(s) in cells of the nervous system. Furthermore, by utilizing tissue or cell specific promoters, selective expression of foreign gene(s) can be maintained in cells of interest. Also, promoters could be utilized which are drug-inducible.

The invention also concerns a method for treating a neurological deficiency of the central nervous system by expressing a gene sequence, which complements the deficiency, in a cell in the central nervous system by introducing a HSV-1 vector with a mutation in a gene for viral replication and with a gene sequence downstream of a promoter sequence so that the gene sequence will be expressed in the cell and the expressed gene product complements the deficiency.

The invention is further directed to methods for modulating neuronal physiology by delivery of neuropeptide genes, such as those genes that express proteins or polypeptides to block pain including, for example, analgesic neuropeptides; genes that express growth factors including, for example, nerve growth factor; genes that express proteins or polypeptides to promote regeneration or prolong the life-span of a cell including, for example, superoxide dismutase; genes that express toxic proteins or polypeptides including, for example, ricin A, diphtheria toxin, and tetanus toxin, for example to kill tumor cells or to cause a cell-specific injury.

In the methods for modulating neuronal physiology, the method comprises introducing into a cell a HSV-1 vector with a mutation in a gene for viral replication and with a gene sequence coding for the desired protein or polypeptide located downstream of a promoter sequence so that the gene sequence will be expressed in the cell and upon expression will modulate the neuronal physiology.

The invention further concerns a method for treating persistent pain associated with nerve injury by expressing an analgesic neuropeptide gene sequence in a sensory neuron or in central nervous system neurons, by introducing a HSV-1 vector with a mutation in a gene for viral replication and with a gene sequence downstream of a promoter sequence so that the gene sequence is expressed in the cell and the expressed gene product substantially eliminates pain. In addition, vectors capable of causing a cell specific injury can also be used to relieve pain.

The present invention also relates to an animal model for painful neuropathy and a method for producing such an animal model. The animal model is produced by expressing a toxic gene sequence in a sensory neuron, wherein the expressed gene product causes cellular injury which injury results in painful neuropathy.

Enkephalin containing or other opioid peptide gene vectors can be introduced into regions of the central nervous system to induce analgesia (for example, periaquaductal grey). In addition, vectors capable of causing a cell specific injury can also be used to relieve pain in the present animal models.

The present invention further relates to an animal model for nervous system disease.

The methods and vectors of the invention can also be used to insert antisense sequences or ribozymes to reduce the expression of an endogenous protein associated with toxicity.

DESCRIPTION OF THE PREFERRED EMBODIMENTS

Definitions

Figure 1:
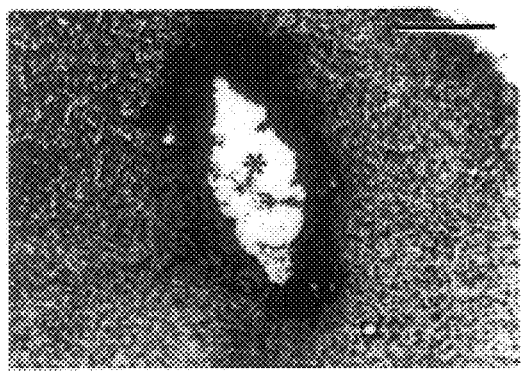
FIG. 1 shows photomicrographs illustrating β-galactosidase expression in rat brain cells after injection with herpes simplex virus vectors 7134 and RH105 after 1 day, 3 days, and 14 days.
Figure 1:
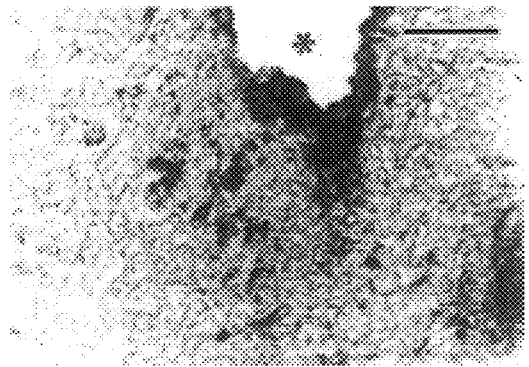
Figure 1:
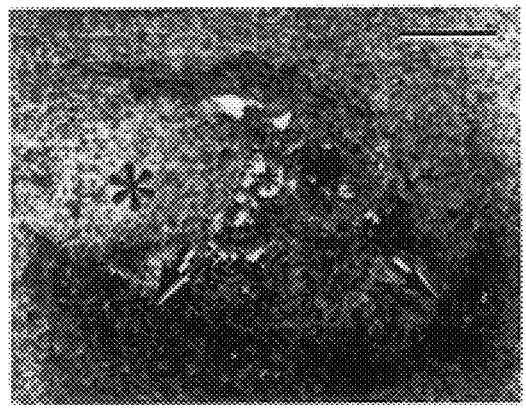
Figure 1:
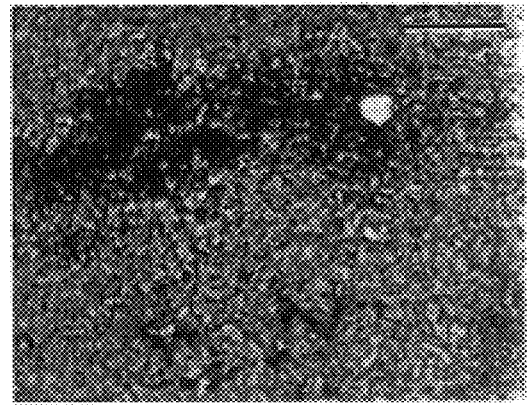
Figure 1:
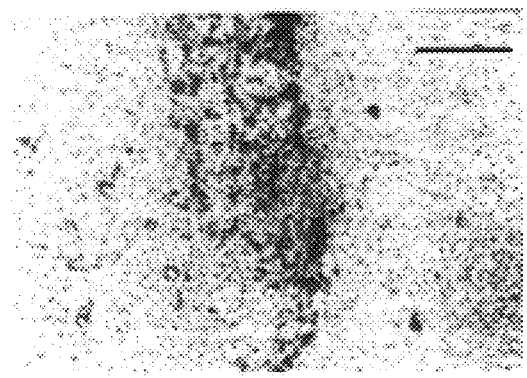
Figure 1:
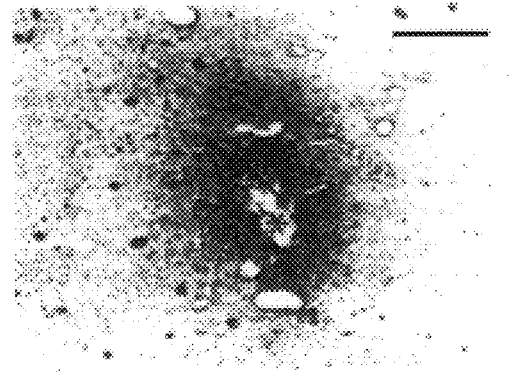

Painful neuropathy. By the term "painful neuropathy" is intended any painful condition characterized by persistent pain in human and animal; caused. by nerve injury in, for example, nervous system diseases, including for example, causalgia, trigeminal neuralgia, and painful diabetic neuropathy; as well as painful conditions such as post-herpetic neuralgia which follows varicella zoster infection, and painful conditions caused by acquired immunodeficiency syndrome (AIDS painful neuropathy).

Persistent Pain. By the term "persistent pain" is intended pain that is severe, disabling, and refractory to standard pharmacological or surgical interventions.

Sensory neuron. By the term "sensory neuron" is intended any nerve cell that receives input from the environment that is transduced into electrical and chemical signals that are conducted from the peripheral to the central nervous system.

Animal. By the term "animal" is intended any living creature especially any mammal, including for example the rat, mouse, hamster, guinea pig, primate, rabbit and human.

Animal Model. By the term "animal model" is intended the analog in an animal (animal as defined above excluding a human) of a nervous system disease or painful neuropathy in man.

Painful neuropathy in humans can arise from nerve injury in conditions including for example causalgia, trigeminal neuralgia and painful diabetic neuropathy, as well as painful conditions including for example, post-herpetic neuralgia and painful neuropathy in AIDS patients.

The present animal model is produced by introducing into a cell of an animal a toxic gene sequence whose gene product disrupts the function of neurons, thereby producing the animal model. For example, an animal model for painful neuropathy, as well as an animal model for nervous system disease, can be produced.

Regarding painful neuropathy, an animal model for painful neuropathy can be produced by introducing a toxic gene sequence into a sensory neuron wherein the toxic gene product causes nerve injury which injury results in painful neuropathy. Such nerve injury includes for example, cell-specific injuries which are analogous to nerve injury in man in conditions such as causalgia, trigeminal neuralgia and painful diabetic neuropathy, and to painful neuropathy in man in conditions including for example, post-herpetic neuralgia and painful neuropathy in AIDS patients.

Animal models for nervous system diseases including for example, Parkinson's disease, Alzheimer's disease and Huntington's disease, can be produced by introducing toxic gene sequences including for example, genes encoding ricin, glutamate, and hydroxydopamine. For example, an animal model for Parkinson's disease can be produced by introducing and expressing a toxic gene sequence encoding hydroxydopamine (6-OHDA), in a brain cell.

The present animal model exhibits conditions (such as painful neuropathy) which mimic conditions in humans in for example, nerve injury and nervous system disease.

The present animal model is consistently reproducible and allows the development of therapeutic and preventative strategies.

Suitable toxic gene sequences include those which encode for example, ricin, glutamate and hydroxydopamine. The selection of other suitable toxic gene sequences is within the knowledge of one of ordinary skill in the art.

Substantially eliminates. Pain is "substantially eliminated" if an animal suffering from painful neuropathy is free from persistent pain. For example, in humans pain is "substantially eliminated" if the pain is no longer severe, no longer disabling, or no longer refractory to standard pharmacological or surgical interventions. Whether or not pain is no longer severe can be determined by direct communication in the case of a human. Regarding animals, pain is "substantially eliminated" if an animal with for example, peripheral neuropathy has a reduction in its response to pain or reduction in a painful behavior which accompanies such neuropathy (i.e., reduction in a protective behavior such as guarding behavior, and/or a reduction in an exaggerated response) or by a change in behavior of an animal consistent with pain relief. Such determinations can readily be made by one of ordinary skill in the art.

Gene Product. By the terminology "gene product" is intended proteins encoded by a particular gene and/or transcription products of a gene.

Opioid. By the term "opioid" is intended any agent that resembles an opiate in action but is not necessarily derived from opium. Opioids are analgesic neuropeptides, and include for example, the endogenous opiates dynorphin and enkephalin.

Treatment or Treating. By the term "treatment" or "treating" is intended, for the purposes of this invention, that the symptoms of the disorder and/or origin of the disorder be prevented, ameliorated or completely eliminated.

Replication defective. By the terminology "replication defective" is intended mutated viral vectors which do not replicate in neurons.

Cell specific injury. By the terminology "cell specific injury" is intended injury that targets a specific population of neuronal cells.

Analgesic neuropeptide. By the terminology "analgesic neuropeptide" is intended a peptide that relieves pain associated with the nervous system, by altering perception of nociceptive stimuli without producing anesthesia or loss of consciousness. Such peptides include for example, opioids. Other analgesic neuropeptides include galanin and cholecystokinin.

Using HSV-1 vectors that have mutations in genes necessary for efficient viral replication, the inventors have discovered methods for introducing and expressing a gene sequence in cells of the nervous system, for example, in cells of the central and peripheral nervous system without toxicity to the host animal. Cells of the peripheral nervous system include, for example, cells of the somatosensory system, such as sensory neurons, including for example, sensory neurons of the trigeminal ganglia, motor neurons, Schwann cells.

HSV-1 is a double-stranded DNA virus which is replicated and transcribed in the nucleus of the cell.

In virions, HSV-1 vectors are composed of head to tail repeats. (Stow et al., *Eukaryotic Viral Vectors,* Y. Gluzman, Ed. (Cold Spring Harbor Laboratory, Cold Spring Harbor, N.Y., 1982), pp. 199–204; Spaete et al., *Cell* 30:285 (1982).) HSV-1 contains approximately 70 genes and is approximately 150 kilobases in size. Five immediate early ("IE") genes encode infected cell proteins (ICPs) 0, 4, 22, 27, and 47, the major regulatory proteins of the virus. These immediate early proteins then act to regulate the expression of viral proteins of the early (E) and late (L) classes. Proteins of the E class are responsible for viral DNA replication. The late ("L") genes are induced after DNA replication and encode the structural components and enzymes required for assembly of virus particles. When the late genes are induced, transcription of the immediate early genes is reduced.

Post-mitotic neurons harbor HSV-1 in the virus' latent state (Stevens, J.G., *Curr. Top. Microbiol. Immunol.* 70:31–50 (1975).) Once HSV-1 attains latency, it can be retained for the life of the neuron. Latent HSV-1 is capable of expressing genes. Expression of a gene encoded by HSV-1 has been detected by in vitro hybridization in latently infected neurons. Furthermore, HSV-1 is transported both anterogradely and retrogradely in neurons, and can be passed transsynaptically. These properties are especially advantageous in that it suggests that HSV-1 vectors will be capable of reaching targets of interest some distance away from the injection site.

Two lines of evidence suggest that HSV-1 can infect most, if not all, kinds of neurons in the central and peripheral nervous systems. First, regarding the central nervous system following inoculation of HSV-1 in the periphery, a burst of virus production ascends the neuraxis, initially in the sensory or motor neurons innervating the site of inoculation, then in the spinal cord, brain stem, cerebellum, and cerebral cortex (Koprowski, H., In: *Persistent Viruses* (Stevens, F. G., ed.), pp. 691–699, Academic Press, N.Y. (1978).) Second, attempts to mimic HSV-1 latency in tissue culture with different preparations of neurons have required high temperature, DNA synthesis inhibitors, and antisera directed against HSV-1 virions to prevent a lytic infection from spreading to all the neurons (Wigdahl et al., *Proc. Natl. Acad. Sci. USA* 81:6217–6201 (1984).)

In the method according to this invention, HSV-1 vectors with mutations in genes involved in viral replication can be used to effect gene delivery to cells in the nervous system, for example, in cells of the central and peripheral nervous systems. As used herein, the term HSV-1 vectors, or mutated HSV-1, is meant to include viral HSV-1 in which the viral sequences have been directly modified so that it may be used for a vector for gene delivery. The term "mutations in genes involved in viral replication" is meant to include gene deletions, gene deficiencies, gene activation, and the like." As stated above, genes that are involved in viral replication that may be mutated in this invention include the five immediate-early (IE) viral genes encoding regulatory infected cell proteins (ICPs) 0, 4, 22, 27, and 47. These genes are described in detail in Longnecker et al., In: *Viral Vectors,* Gluzman et al. (eds.), CSH Lab, pp. 68–72 (1988); Roizmann et al., In: *Virology,* Fields et al. (eds.), Raven Press, N.Y., pp. 497–526 (1985); Rock et al., *Nature* 302:523–525 (1983).

The delivery of functional genes to the nervous system offers a potential form of treatment of a variety of neurologic conditions (Geller et al., *Proc. Soc. Neurosci.* 17:240.12 (1991); Martuza et al., *Science* 252:854–856 (1991); Breakefield et al., Fond. IPSEN Proc. (in press)). Such conditions include, for example neurodegenerative disorders and pain syndromes. In addition, the delivery of toxic genes which alter the physiology of neurons (disrupts the function of neurons), may be used to produce animal models of neurologic disease. For example, animal models which mimic human conditions of nervous system disease can be produced. Suitable toxic genes include genes encoding ricin, glutamate, and hydroxydopamine (6-OHDA). Genes can be delivered to mimic nervous system diseases including for example, Parkinson's disease, Alzheimer's disease and Huntington's disease. For example, a gene for mutant amyloid protein can be delivered to produce an animal model of Alzheimer's disease. The selection of other suitable genes is within the knowledge of one of ordinary skill in the art.

In the somatosensory system, analgesic neuropeptide genes can be delivered to sensory neurons to treat painful neuropathy. That is, to relieve the persistent pain which follows nerve injury in conditions such as causalgia (Livingston, W. K., *Pain Mechanisms:*91–93, New York, MacMillan (1943)), trigeminal neuralgia (Fromm, G. H., *Pain: Mechanisms and syndromes, In: Neurologic Clinics of North America:*305–319, Philadelphia, W. B. Saunders (1989)), herpetis infection, partial nerve transection, and painful diabetic neuropathy (Thomas et al., *Peripheral Neuropathy.:*1773–1811, Philadelphia, W. B. Saunders (1984)). Suitable analgesic neuropeptides include for example, peptides including dynorphin, enkephalin, galanin and cholecystokinin. The selection of other suitable analgesic neuropeptides is within the knowledge of one of ordinary skill in the art to which the present invention pertains.

Other types of genes can also be delivered to sensory neurons to reduce pain. For example, a gene sequence for antisense RNA or ribozymes under a strong promoter including for example, CMV and RSV, can be delivered to sensory neurons to decrease synthesis of the neurotransmitter released by sensory neurons in the spinal cord, i.e., antisense to the mRNA for neuromodulating neuropeptides including substance P (a neuromodulating neuropeptide), (DeKoninck, Y. and Henry, J. L., *Proc. Natl. Acad. Sci. USA* 88:11366–11348 (1991)). Genes for other antisense molecules can be selected and utilized to block synthesis of neurotransmitters other than the neurotransmitter substance P. Suitable gene sequences encoding neurotransmitters include all gene sequences for neurotransmitters used by nocioceptive neurons. The selection of suitable gene sequences for antisense RNA and for neurotransmitters is within the knowledge of one of ordinary skill in the art to which the present invention pertains.

Gene sequences encoding peptides which serve as antagonists for neurotransmitters including the neurotransmitter substance P, can be delivered to sensory neurons. Suitable gene sequences include those encoding, for example, the antagonist peptides set forth in Calcagnett, D. S. et al., *Peptides* 10:319–326 (1989). Such antagonists are incorporated into a precursor protein, which then allows processing and incorporation of the antagonist into secretory vesicles. Gene sequences for recombinant peptides which encode the ligand domain of antibodies that bind to substance P or other neurotransmitters, can also be used as antagonists. The selection of other suitable gene sequences encoding antagonists is within the knowledge of one of ordinary skill in the art. For example, suitable antagonists include L-amines and peptides.

Also, the present method can be used to model human painful conditions by delivering genes including for example, the toxic genes noted above, to sensory neurons in experimental animals to produce a cell-specific injury. Such injury to somatosensory neurons in humans is associated with long term changes in nociceptive pathways (Wall, P. D., *Advances in Pain Research and Therapy,* New York, Raven Press (1983); Tasker, R. R., *Textbook of Pain:*119–133, London, Churchill, Livingstone (1984); Woolf, C. J., *J. Neurosci.* 34:465–478 (1990); Woolf, et al., *Nature* 355 (6355):75–78 (1992)), and persistent pain (Wynn-Parry, C. B., *Advances in Pain Research and Therapy,* New York, Raven Press (1983); Zimmerman, M., *Advances in Pain Research and Therapy,* New York, Raven Press (1983)) that is severe, disabling and refractory to standard pharmacologic or surgical interventions (White et al., *Pain and the Neurosurgeon: A Forty Year Experience,* Springfield, Ill., Charles C. Thomas (1969); Fields, H. L., *Pain:*285–307, New York, McGraw Hill (1987)). The ability to produce a cell-specific injury in animals that is associated with a change in pain behavior will lead to a better understanding of human painful conditions such as post-herpetic neuralgia, which follows varicella zoster infection (Watson, C. P. N., *Pain: Mechanisms and syndromes, In: Neurologic Clinics of North America:*231–248, Philadelphia, W. B. Saunders (1989)), or painful neuropathy in patients with acquired immunodeficiency syndrome (AIDS) (Cornblath et al., *Neurology* 38:794–796 (1988)).

Thymidine kinase deficient (TK$^-$) viruses are useful vectors for gene delivery to cells of the nervous system including cells of the central and peripheral nervous system, such as sensory neurons, since they are incapable of primary or secondary lytic infection, but are able to enter latency and confer long term stable expression of foreign genes in these neurons.

The preferred mutated HSV-1 virus vectors are those that enter latency in neurons and do not reactivate or reactivate very inefficiently.

The present invention concerns a means for in vivo introduction of gene sequences into cells of the nervous system, for example, into cells of the central and peripheral nervous system. The cells of the central nervous system include primarily neurons, but also include neuroglia and other cells. The cells of the peripheral nervous system include primarily neurons, including for example, neurons of the somatosensory system such as neurons from the trigeminal ganglia. These cells are collectively described herein as "neural or neuronal" cells. Neural cells are described, for example, by Barr, M. L., *The Human Nervous System An Anatomic Viewpoint,* 3rd. Ed., Harper & Row, NY (1979), which reference is herein incorporated by reference.

The term "gene sequence," as used herein, is intended to refer to a nucleic acid molecule (preferably DNA). Such gene sequences may be derived from a variety of sources including DNA, cDNA, synthetic DNA, RNA, or combinations thereof. Such gene sequences may comprise genomic DNA which may or may not include naturally occurring introns. Moreover, such genomic DNA may be obtained in association with promoter regions or poly A sequences. The gene sequences of the present invention are preferably cDNA. Genomic DNA or cDNA may be obtained in any of several ways. Genomic DNA can be extracted and purified from suitable cells by means well-known in the art. Alternatively, mRNA can be isolated from a cell and used to produce cDNA by reverse transcription, or other means.

As will be appreciated by one of ordinary skill, the nucleotide sequence(s) of the inserted gene sequence or sequences may be of any nucleotide sequence.

The desired gene sequence is operably linked, and under the control of a promoter sequence so that the gene sequence will be expressed in the host cell. The promoter sequence is one that affects expression of the gene sequence and which can be a viral promoter active during latency to drive stable expression of foreign genes in sensory neurons. (Dobson et al., *J. Virol.* 63:3844–3851 (1989); Ho et al., *Proc. Natl. Acad. Sci. USA* 86:7596–7600 (1989).) Since herpes virus is known to be maintained in a latent state in the brain, the promoter for the latency-associated transcript (LAT) may be used to mediate stable gene expression. Further, the promoters for the genes for viral replication can be used as promoters to express the gene sequence.

The invention is further drawn to the use of non-viral, mammalian promoters to drive long term expression of a gene sequence in viral infected cells. The gene sequence may be homologous or heterologous with respect to the operably linked promoter sequence. That is, the mammalian promoters of the invention continue to drive expression of the foreign gene during viral latency. Mammalian promoters of particular interest include those which drive expression in cells including neuronal specific enolase promoter (pNSE) (Forss-Peters et al. (1990)), general neuronal promoters such as neurofilament (NF) (Gulien et al., *Genes and Develop.* 1:1085–1095 (1987)); thy-1 promoter (Chen et al., *Cell* 51:7–19 (1987)), etc. Likewise, promoters which drive expression of a gene in subpopulations of neural cells such as tyrosine hydroxylase promoter (TH) (See *Nucl. Acids. Res.* 15:2363–2384 (1987) and *Neuron* 6:583–594 (1991)); GnRH (Radovick et al., *Proc. Natl. Acad. Sci. USA* 88:3402–3406 (1991)); L7 (Oberdick et al., *Science* 248:223–226 (1990)); DNMT (Bartge et al., *Proc. Natl. Acad. Sci. USA* 85:3648–3652 (1988)), enkephalin promoter (Comb et al., *EMBO J.* 17:3793–3805 (1988)); GFAP; MBP; and the like can be utilized. It is recognized that the ability of a cell-specific promoter may be dependent on two criteria. These criteria include: the regulatory elements present in the promoter itself and how these regulatory elements interact with viral proteins; and, where the promoter is incorporated into the HSV-1 genome.

There is evidence to suggest that other non-dividing cell types besides neurons may be able to express foreign proteins in a long-term and stable manner in the context of a herpes vector including CNS, glial, adrenal, medulla, and muscle cells (See Stevens, J. G., *Microbiol. Rev.* 53:318–332 (1989)). Therefore, other cell-specific promoters that drive expression of a gene in a specific population of non-neuronal cells may be utilized including: glial fibrillary acidic protein (GFAP) (Miura et al., *J. Neurochem.* 55:1180–1187 (1990)); myelin basic protein (MP) (*Neuron* 1:535–543); JC virus (Small et al., *Cell* 46:13–18 (1986)). General promoters include beta-actin (Gunning et al., *Proc. Natl. Acad. Sci. USA* 84:4831–4835 (1987)); metallothionin (MT) (Morahan et al., *Proc. Natl. Acad. Sci. USA* 86:3782–3786 (1991)); polyoma large T antigen (Bohnhein et al., *Nucl. Acids Res.* 13:4789–4796 (1985)); adenosine deaminase (Valerio et al., *Nucl. Acids Res.* 16:10083–10097 (1988)); SV40 large T antigen (Palmiter et al., *Nature* 316:457–460 (1985)); Rous sarcoma virus LTR (Gorman et al., *Proc. Natl. Acad. Sci. USA* 79:6777 (1982)).

Cellular promoters of interest can be tested by their ability to express the *E. coli* lacZ gene. LacZ is a useful marker gene because it is detectable by histochemical means, it can be distinguished from the mammalian enzyme by its higher pH optimum, and antibodies against the bacterial protein can be utilized to examine levels of the enzyme produced in neuronal cells. See, Ho et al. *Virology* 167:279–283 (1988).

It is recognized that the promoter and gene sequence it controls may be inserted into various sites of the viral genome. However, it is preferable to integrate the promoter/gene sequence construct into the HSV-thymidine kinase gene. The thymidine kinase gene is an attractive site for integration of the construct for several reasons. First, because thymidine kinase is dispensable for viral replication in most dividing cells, the altered virus can be grown and maintained in culture. Secondly, drugs like acyclovir and bromovinyl deoxyuridine are available for selection of thymidine kinase mutant (TK⁻) virus. Thirdly, the loss of thymidine kinase renders HSV replication-defective in neurons. Furthermore, because there is only one thymidine kinase locus within the HSV-1 genome, integration into only a single site is required to render the virus thymidine kinase defective (TK⁻). Lastly, the mutant TK⁻ virus is able to enter latency, but the virus cannot reactivate from this state. See, Leist et al. *J. Virology* 63:4976–4978 (1989).

Thus, viral vectors of the invention include HSV replication deficient vectors having viral and nonviral promoters, including mammalian promoters. Those vectors having mammalian promoters will comprise a mammalian promoter operably linked to a gene sequence of interest. By replication deficient is intended that the viral vector is unable to replicate in target cells. As discussed above, mutations or inserts into genes involved in viral replication will render the virus unable to replicate.

A viral vector, as that term is used herein, is a nucleic acid molecule (preferably of DNA) in which a gene sequence (which is to be transferred) is fused to a subset of viral sequences which are capable of expressing the gene. Also, the viral vector according to this invention will have a mutation in a gene necessary for efficient viral replication. The viral vector should also not have deleterious effects on the host and should infect cells without a helper virus. The viral sequences and the total genome size is selected such that the vector is capable of being encapsulated in a virus particle and thus be capable of binding to, and introducing its gene sequences into a virus-sensitive host cell.

The HSV-1 mutant viral vectors of the present invention can be obtained by transfecting permissive cells with a mixture of plasmid DNA containing HSV-1 gene deletions and infectious HSV-1 DNA. Stow et al., *Eukaryotic Viral Vectors*, Y. Gluzman, Ed. (Cold Spring Harbor Laboratory, Cold Spring Harbor, N.Y., 1982), pp. 199–204; Spaete et al., *Cell* 30:285 (1982). The obtained mutated HSV-1 viral vectors can be propagated as viruses in appropriate host cells. To grow most mutants, one must transfect a cell with the mutated (and missing) viral gene to replace the deleted viral replication function.

Injection of the vectors to express the desired gene sequence may be done in virtually any part of the body, including muscle, adrenal medullary cells, brain, spinal cord, nerve endings in the skin, blood vessels, ventricular surface, etc. Many types of non-dividing cells may harbor the virus in stable fashion. See, Stevens, J. G., *Adv. Cancer Res.* 26:227–256 (1978) and Stevens, J. G., *Microbiol. Rev.* 53:318–332. The virus is provided for injection in a concentration in the range of about $10^1$ to about $10^{10}$ plaque forming units (PFU)/ml, more generally in the range of about $2\times10^5$ to about $1\times10^8$ PFU/ml.

Gene transfer technology has several applications to neuroscience and neurochemistry. The most immediate applications are, perhaps, in elucidating the process of neural peptides and the functional domains of proteins. Cloned cDNA or genomic sequences for neural proteins can be introduced in vivo in order to study cell type-specific differences in processing and cellular fate. By placing the coding sequences under the control of a strong promoter, a substantial amount of the protein can be made, thus avoiding difficulties in characterizing trace amounts. Furthermore, the specific residues involved in protein processing, intracellular sorting, or biological activity can be determined by mutational change in discrete residues of the coding sequence.

Gene transfer technology can also be applied to provide a method to control expression of a protein and to assess its capacity to modulate cellular events in the nervous system, for example, in the central and peripheral nervous systems. Certain functions of neural proteins can be studied in vivo, for example, at different times in development or aging. in order to monitor changes in receptor density, cell number, fiber growth, electrical activity, neurotransmission, and other relevant properties.

Gene transfer provides a means to study the DNA sequences and cellular factors which regulate expression of neural specific genes. One approach to such a study would be to fuse the regulatory elements to be studied to a particular reporter gene and subsequently assaying for the expression of the reporter gene.

The regulation of gene expression in neuronal cells has been found to have a role in maintaining homeostasis and is believed to have a role in mediating information retention in response to external and internal signals (Black et al., *Science* 236:1263–1268 (1987)). During development, coordinate regulation of gene expression serves to produce a differentiated phenotype, e.g., as in catecholamine metabolism and myelin biosynthesis. Regulation depends on many factors including chromatin structure, DNA methylation, and trans-acting factors, which respond to phosphorylation, hormones, and other signals. It is a complex process that allows sets of genes to be expressed together or differentially and may involve a combinatorial code of regulatory sequences.

Issues of cellular fate and interactions in the nervous system including the central and peripheral nervous systems can also be addressed by gene transfer. For example, genes which encode histological markers can be introduced into embryonic cells to determine lineage relationships during development and to elucidate neuronal pathways and to follow cell maturation and fate. In addition, genes encoding growth factors, oncogenic proteins, toxic peptides, or other physiologically important proteins, can be introduced into specific areas of the central nervous system, such as the brain and spinal cord or into areas of the peripheral nervous system, for example into sensory neurons, to study their effects on cell division, survival, and differentiation. For some studies, gene transfer or gene expression must be restricted to specific cells in the nervous system.

Such methods of the invention can also be used to express sequence, which encode antisense messages to reduce the expression of endogenous gene(s) associated with toxicity, e.g., antisense to amyloid precursor protein that accumulates in Alzheimer's disease.

Gene transfer also possesses substantial potential use in understanding and providing therapy for disease states. There are a number of inherited neurologic diseases in which defective genes are known and have been cloned. In some cases, the function of these cloned genes is known. In humans, genes for defective proteins have been identified for (1) lysosomal storage diseases such as those involving β-hexosaminidase (Kornerluk et al., *J. Biol. Chem.* 261:8407–8413 (1986); Myerowitz et al., *Proc. Natl. Acad. Sci. USA* 82:7830–7834 (1985)) and glucocerebrosidase (Sorge et al., *Proc. Natl. Acad. Sci. USA* 82:5442–5445 (1985); Tsuji et al., *N. Engl. J. Med.* 316:570–575 (1987)), (2) for deficiencies in hypoxanthine phosphoribosyl transferase activity (the "Lesch-Nyhan" syndrome; Stout et al., *Met. Enzymol.* 151:519–530 (1987)), (3) for amyloid polyneuropathies (prealbumin; Sasaki et al., *Biochem. Biophys. Res. Commun.* 125:636–642 (1984), (4) for Alzheimer amyloid (Tanzi et al., *Science* 235:880–884 (1987); Goldgaber et al., *Science* 235:877–880 (1986)); (5) for Duchenne's muscular dystrophy (uncharacterized muscle protein; Monaco et al., *Nature* 323:646–650 (1987)); and (6) for retinoblastoma (uncharacterized protein expressed in the retina and other tissues, Lee et al., *Science* 235:1394–1399 (1987); Friend et al., *Nature* 323:643–646 (1986).)

Gene transfer techniques can also be used to study the "shiverer" mutation (myelin basic protein, Roach et al., *Cell* 42:149–155 (1987); Molineaux et al., *Proc. Natl. Acad. Sci. USA* 83:7542–7546 (1986)) and the "jimpy" mutation (proteolipoprotein, Nave et al., *Proc. Natl. Acad. Sci. USA* 83:9264–9268 (1986); Hudson et al., *Proc. Natl. Acad. Sci. USA* 84:1454–1458 (1987).)

The above diseases fall into two classes: deficiency states, usually of enzymes, which are inherited in a recessive manner; and unbalanced states, at least sometimes involving structural or regulatory proteins, which are inherited in a dominant manner.

For deficiency state diseases, gene transfer could be used to bring a normal gene into affected tissues for replacement therapy, as well as to create animal models for the disease using antisense mutations. For unbalanced state diseases, gene transfer could be used to create the disease state in a model system, which could be used in efforts to counteract the effect of the imbalance. Thus, the methods of the present invention permit the treatment of neurological diseases. As used herein, a deficiency state disease is "treated" by partially or wholly remedying the deficiency which causes the deficiency or which makes it more severe. As used herein, an unbalanced state disease is "treated" by partially or wholly remedying the imbalance which causes the disease or which makes it more severe.

Further, the methods of the invention can be used to treat a dominant condition by expression of antisense nucleic acid to block the expression of mutant protein. Alternatively, the method could be used to introduce and overexpress the gene encoding the normal protein to "swamp out" and alleviate the effects of the mutant protein.

The method of this invention may also be used to modulate normal physiologic processes, e.g., delivery of growth factors or other peptides or enzymes to optimize neural regeneration after injury or prolong cell survival in aging or after toxic insults. In addition, it can be used to regulate transmission across certain synapses, for example, to kill neurons in the pathway, or alter neurons within phenotype by up or down regulation of normal neuropeptides or producing neuropeptide analogs as in pain transmission, control of blood pressure, and modulation of behavior.

In summary, this invention provides a framework for construction and use of replication deficient HSV-1 vectors that can mediate delivery and expression of genes in neurons and other cells in the nervous system, for example cells in the central nervous system, such cells in the brain and spinal cord, and in cells of the peripheral nervous system. Virus mutants which cannot replicate in neurons, but can still enter latency, provide the safest vehicle for delivery and appear optimal for targeted delivery to individual neurons either to effect changes in their physiology or to trace their extensions. Mutants which undergo limited replication can be used to alter the physiology of larger groups of neurons and possibly even through transfer across synapses. Such mutants, however, may be somewhat pathogenic, as cells harboring productive infections may be killed. Herpes vectors thus offer the potential to alter the physiology of single or groups of neurons to study their function and also provide an avenue of exploration for therapeutic interventions aimed at correcting defects and modulating in neuronal functions.

Having now generally described this invention, the same will be better understood by reference to certain specific examples which are included herein for purposes of illustration only and are not intended to be limiting of the invention, unless specified.

EXAMPLES

Introduction

Four mutant viruses were studied to explore the potential of these replication deficient mutants as vectors to deliver genes in CNS cells in vivo.

The first vector, 7134, provided by Drs. Priscilla Schaffer and Weizhong Cai (Dana Farber Cancer Center) possesses lacZ substitutions in both copies the of HSV-1 ICP0 gene. The construction of this vector is described in detail in Cai et al., *J. Virol.* 63:4579 (1989), incorporated herein by reference. Expression of lacZ in this mutant is regulated by the ICP0 immediate-early promoter. Compared to wild-type HSV-1, ICP0 mutants replicate poorly in a variety of cells in culture and in vivo. These mutants establish latency in sensory neurons of trigeminal ganglia, when used to inoculate mouse corneas. Once they have established latency, however, they reactivate very inefficiently. (Leib et al., *J. Virol.* 63:759–768 (1989); Sacks et al., *J. Virol.* 61:829–839 (1987).)

The second vector, GAL4, provided by Dr. Neal DeLuca, possesses lacZ substitutions in both copies of the ICP4 gene. This vector is described in detail in Shepard et al., *J. Virol.* 63:3714 (1989), incorporated herein by reference. Expression of lacZ is controlled by the early promoter for the ICP6 gene. ICP4 mutants do not replicate in culture or when inoculated onto mouse corneas. As a consequence, ICP4 mutants are unable to establish latency efficiently, and cannot reactivate from the latency state. (DeLuca et al., *J. Virol.* 62:732–743 (1988); Leib et al., *J. Virol.* 63:759–768 (1989).)

The third vector, RH105, provided by Drs. Edward Mocarski and Dora Ho (Stanford) contains a lacZ substitution in the thymidine kinase gene. This vector is described in detail in Ho et al., *Virology* 167:279 (1988), incorporated herein by reference. Expression of this gene is regulated by the ICP4 immediate-arly promoter. Thymidine kinase (TK) gene is described in Palella et al., *Gene* 80:138 (1989); Coen et al., *Proc. Natl. Acad. Sci. USA* 86:4736 (1989); Ho et al., *Virol.* 167:279 (1988). TK mutants can replicate in actively growing cells in culture (presumably by utilizing the endogenous cellular thymidine kinase), but replicate poorly following inoculation peripherally or in nervous system cells into rodents. (Leist et al., *J. Virol.* 63:4976 (1989); Coen et al., *Proc. Natl. Acad. Sci. USA* 86:4736 (1989).) These mutants can enter latency in sensory neurons of peripheral ganglia, but do not reactivate from the latent state. (Leist et al., *J. Virol.* 63:4976 (1989); Coen et al., *Proc. Natl. Acad. Sci. USA* 86:4736 (1989).)

Previous animal studies with similar mutant viruses have shown that they are relatively nonpathogenic. (Ho et al., *Virology* 167:279 (1988); Coen et al., *Proc. Natl. Acad. Sci. USA* 86:4736 (1989); Leib et al., *J. Virol.* 63:759 (1989).) However, these experiments were based on inoculation of epidermal tissues (corneas or footpads) and histological assessment of infections in the sensory ganglia of the peripheral nervous system. Thymidine kinase deficient viruses are known to be relatively non-pathogenic in the central nervous system as well. See, for example, Field and Wildy, *J. Hyg.* 81:267 (1978).

These three vectors, 7134, GAL4, and RH105, were used to express the Escherichia coli lacZ gene in neuronal cells of rat central nervous system. These vectors possessed lacZ deletional substitutions in the genes encoding the immediate-early viral proteins, ICP0 and ICP4, and the early protein, thymidine kinase, and consequently were compromised or defective in their ability to replicate. In all cases lacZ was placed under immediate-early or early viral promoters active in the early phase of infections. Expression of β-galactosidase was observed in cortical neurons following stereotactic inoculation of these mutant viruses into adult rat brains. All mutant vectors exhibited markedly reduced pathogenesis in animals as compared to wild type HSV-1 KOS strain.

Different patterns of expression of the β-galactosidase gene were observed with the different vectors used. Injection of the ICP0 mutant in frontal cortex and caudate produced β-galactosidase expression in a substantial number of cells around the inoculation site and at some distance from it for up to 14 days. The ICP0 vector appeared to have been transported retrogradely to the contralateral cingulate cortex. The ICP4 and thymidine kinase mutants showed only a few cells expressing β-galactosidase cells in brain areas immediately adjacent to the injection tract for a few days after injections. These herpes virus-derived vectors provide an opportunity for the in situ delivery and expression of specific genes in neurons in the central nervous system (CNS) with little adverse effect on animals.

Example 1

In order to evaluate the potential use of vectors 7134, GAL4, and RH105 for direct gene delivery into CNS cells, the potential pathogenic effects on animals following direct intracerebral inoculations was first assessed. Using 200,000 plaque forming units (PFUs) of 7134, GAL4, RH105, or the wild-type KOS strain of HSV-1 in 2 µl volumes, these vectors were injected into the right frontal area of adult rat brains. As a control, equal volumes of medium alone were injected. Rat survival and behavior were then assessed daily for four weeks. Table I shows the survival results for these animals. While all animals survived for three days without apparent abnormalities, seven of eight rats injected with KOS and one of seven rats injected with 7134 exhibited profound behavioral abnormalities. The rats injected with KOS showed either lethargy or marked hyperactivity after 3 days, had frequent seizures within 4–5 days, and died by 6 days. The animal that did not survive the 7134 injection was lethargic and showed a marked decrease in feeding and drinking activities starting approximately 8 days after injection and its death occurred rapidly thereafter. One animal that received an intracerebral injection of 7134 became lethargic and perished after 8 days. At autopsy, foci of β-galactosidase positive neurons were found dispersed throughout the cerebral cortex, particularly in the temporal lobes. This pattern appeared behaviorally and neuropathologically similar to the one seen in the rats that had received intracerebral injections of the wild-type HSV-1 KOS. (However, wild type did not have blue cells.) Since this particular rat had been housed mistakenly in a cage that contained rats which had been injected with wild-type virus, one possible explanation for the widespread distribution of lacZ positive cells in this animal is that it also became infected with wild-type HSV-1 KOS, presumably through some of the blood and serous fluid found at the craniotomy site. This might have created a helper effect allowing for the widespread replication of 7134 in this animal. Control animals and those injected with GAL4 or RH105 viruses showed no behavioral abnormalities or death over a two-week period. These results indicate that these HSV mutant vectors, GAL4, RH105, and 7134, are relatively nonpathogenic and that behavioral abnormalities do not routinely result from their use in rats. A repeated study with 7134 did not show the anomaly previously exhibited.

Example 2

After inoculations as described in Example 1, rats were sacrificed one, three and fourteen days after virus inoculations in order to assess the extent of β-galactosidase expression. Brains were processed histochemically and assessed for the presence of β-galactosidase activity. In the presence of the substrate X-gal at alkaline pH, this enzyme yields an intense blue stain throughout the cytoplasm of infected cells. (Turner et al., *Nature* 328:131 (1987); Price et al., *Proc. Natl. Acad. Sci. USA* 84:156 (1987); Sanes et al., *EMBO J.* 5:3133 (1986).)

With the aid of a stereotactic apparatus, approximately 200,000 PFUs of each mutant virus were injected into the right frontal area of rat brains (stereotactic coordinates: AP+2.7/LAT−0.3/Depth−0.4). Two µl volumes were injected with a Hamilton syringe using stereotactic coordinates. Rats were then monitored daily for abnormalities in feeding and drinking behavior and for level of activity. One, three, and fourteen days after viral injections, animals were anesthetized and sacrificed by intracardiac perfusion with 200 ml of 3% paraformaldehyde in phosphate buffered saline. Anesthesia was obtained by intraperitoneal injection of 0.5 ml–1 ml of a solution that contained 16.2% nembutal, 10% ethanol, 39.6% polyethylene glycol, 166 mM magnesium sulfate and 4.25% chloral hydrate. Brains were then processed over the following 3 days by serially placing them for approximately 24 hours in the same solution which contained increasing concentrations of sucrose (15%, 20%, and 30%). After freezing on dry ice and storage at 70° C., brains were sectioned on a cryostat in 40 µm sections. After washing with phosphate buffered saline, sections were reacted overnight in a solution containing 0.1% X-Gal, 2 mM magnesium chloride, 35 mM potassium ferrocyanide, 35 mM potassium ferrocyanide, 0.1% sodium deoxycholate and 0.1% NP4.0. After washing in phosphate buffered saline, sections were mounted on glass slides and examined by light microscopy.

Numerous cells expressing β-galactosidase were observed one, three and 14 days after stereotactic injection of 7134 into the right front cortex. While most cells expressing β-galactosidase were localized within a 175 µm$^2$ area around the injection site at day 1, positive cells were found in a 600 µm$^2$ area, and at even greater distances away from the injection site, by day 3. By day 14 there was a diminution in the number of cells expressing β-galactosidase with sparse foci located (100 µm$^2$) around the needle track.

In contrast to the findings for 7134, one and three days after RH105 injection, sparse foci of β-galactosidase expressing cells were present only along the needle track (covering an area of 10 $\mu m^2$), and by 14 days no positive cells could be detected (FIG. 1).

Figure 2:
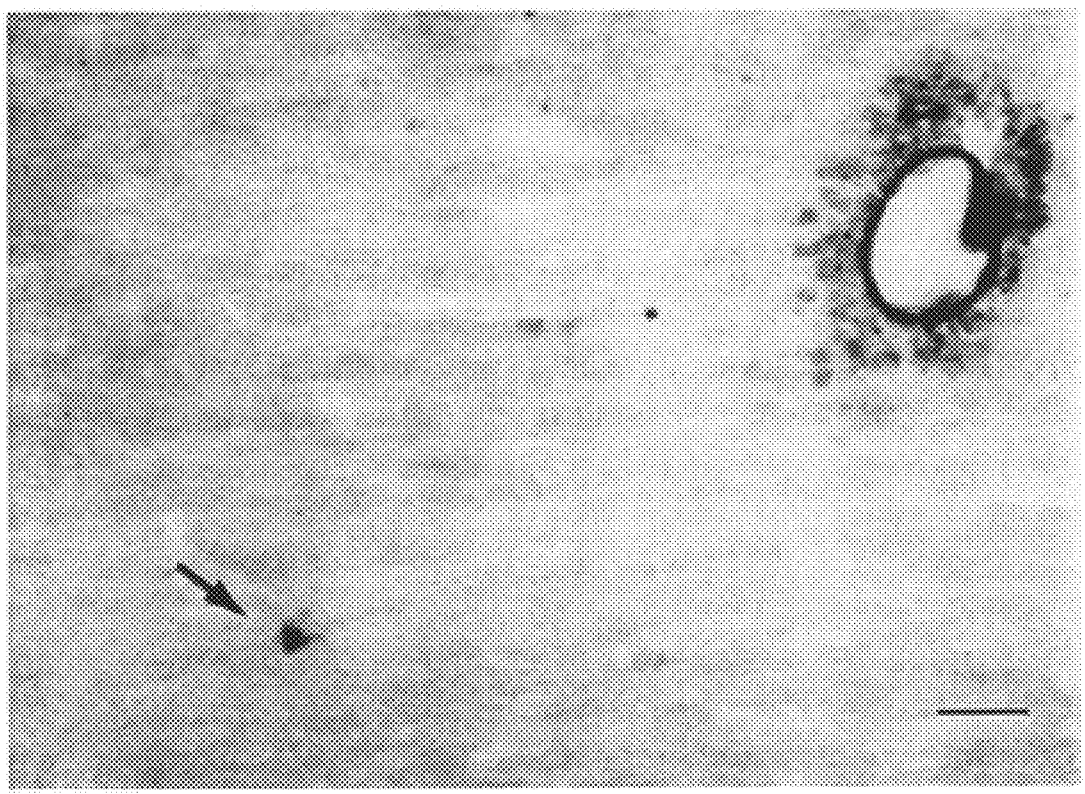
FIG. 2 shows a photomicrograph illustrating β-galactosidase expression in rat brain cells after injection with herpes simplex virus vector GAL4.

Similarly, after GAL4 injection, only an occasional cell expressing β-galactosidase was observed (FIG. 2). Procedures were the same as those discussed above, except that, after the β-galactosidase histochemical reaction, the brain sections were dehydrated in 70% and 80% ethanol and then counterstained with neutral red. Sections were then rinsed in 80% ethanol and water before examining them by light microscopy.

These findings indicate that two patterns of gene delivery are characteristic of these vectors. The first, represented by 7134, is that of a replication compromised vector capable of delivering a gene to a relatively large number of cells in the CNS with limited spread away from the site of a delivery. The second, represented by GAL4 and RH105, is that of a replication defective vector that delivers a gene to only a few cells at the injection site and projecting to it without spread to other sites.

The differences in the patterns of gene expression in the CNS among the vectors could also reflect the inactivation of different viral genes, or genetic differences amongst the viral strains used. Vectors 7134 and GAL4 were obtained from an HSV-1 KOS virus strain that had been propagated in one laboratory, whereas RH105 was derived from an HSV-1 KOS strain propagated in a different laboratory. The wild-type HSV-1 KOS strain used as a control in all experiments was also obtained from the same laboratory that vectors 7134 and GAL4 were obtained.

The differences in the patterns of gene expression in the CNS among the vectors may also reflect variations in promoter strength. This latter possibility is not likely, however, since all three promoters, ICP0 (7134), ICP6 (GAL4), and ICP4 (RH105), are expressed with immediate-early kinetics during productive infection.

The pattern of 7134-mediated β-galactosidase expression is best explained by an initial productive infection in numerous cells near the injection site followed by secondary spread of viral particles to adjacent brain areas. Eventual limit to the spread of this virus could be mediated by decreasing yields of virus from infected cells and entry into latency, and/or by immunosuppression. By contrast, the pattern of RH105 or GALA-mediated β-galactosidase expression indicates that only a small number of cells near the injection site are infected initially, and that no productive infection occurs, although the virus may enter latency.

As controls, brains from rats that had been injected in right frontal areas with the wild-type virus and with medium alone were examined. A monoclonal antibody ID-4 against the major capsid protein of the virus was used to detect infected neurons in rats five days after injection with wild-type HSV-1 KOS. At this time these animals exhibited profound behavioral abnormalities. (In this procedure, the monoclonal antibody ID-4, from the hybridoma cell line (ATCC HB8068) that produced monoclonal antibodies to the HSV-1 viral nucleocapsid was purchased from American Type Culture Collection).

Brain sections from HSV-1 KOS injected rats were rinsed in Tris-buffered-saline (TBS) solution (pH 7.4) and incubated for one hour with horse serum (diluted according to Vectastain ABC kit specifications). The sections were then reacted for one hour with medium harvested from the ID-4 monoclonal antibody producing hybridoma line. After thorough rinsing in TBS, the sections were incubated for one hour with biotinylated horse anti-mouse IgG (Vectastain).

After additional rinsing, the sections were placed for 30 minutes in Vectastain ABC solution, containing avidin and then in a solution containing 0.01% hydrogen peroxide and 0.05% diaminobenzidine tetrahydrochloride in 0.1 M Tris HCP, pH 7.2 for 2–5 minutes. Sections were then rinsed in TBS and mounted on glass slides.

The immunohistochemical reaction detected numerous areas where viral antigen was present at a distance from the injection site. These included bilateral cortical regions in the frontal, cingulate, temporal and parietal lobes. This suggested that the limited number of β-galactosidase expressing cells seen following injection of the mutants is a property of the mutants and is not due to technical artifacts. When medium alone was injected, no blue staining was visible even at higher magnification. This control was necessary due to reports that the β-galactosidase histochemical reaction will at times detect endogenous lysosomal β-galactosidase activity. Ho et al., *Virology* 167:279 (1988).)

Figure 3:
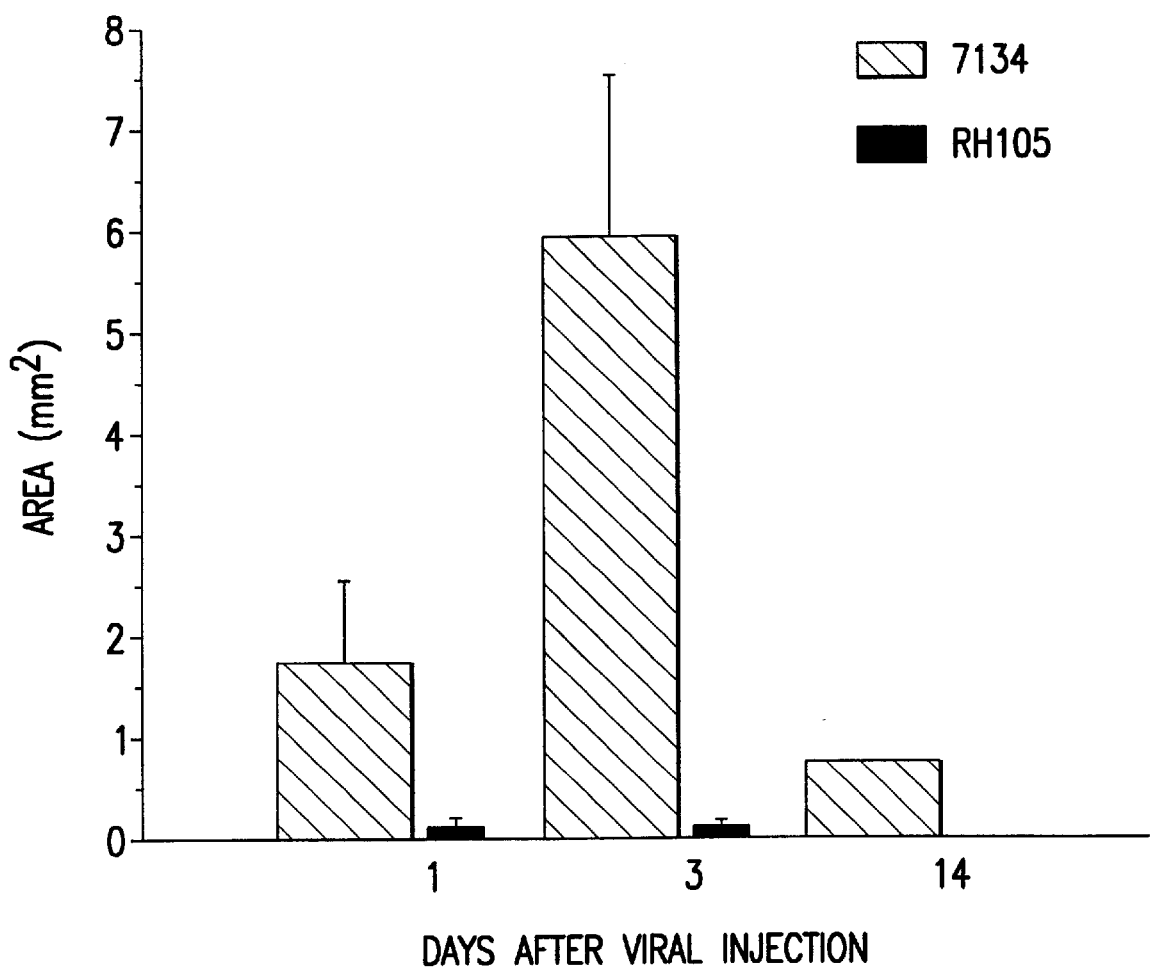
FIG. 3 shows pictures of rat brain areas that contain β-galactosidase expressing cells.

FIG. 3 shows pictures of rat brain areas that contain β-galactosidase expressing cells. Areas along the needle track were calculated by measuring the furthest linear distance between cells expressing β-galactosidase in two perpendicular directions and then multiplying the two values. Several sections (range: 3–11) were measured for each inoculation from at least two different rats (range: 2–4). Error bars indicate S.D. from mean). Bar graphs represent the averages of these measurements. Measurements were taken with the aid of an ocular micrometer on a light microscope.

To determine which type of cells expressed β-galactosidase, following inoculation of 7134 into the right caudate, sections were then examined for β-galactosidase expression after counterstaining with neutral red. Both small and large types of caudate neurons, as identified by morphology, expressed β-galactosidase three days later.

Stereotactic injections of 7134 were performed in the right caudate nucleus (stereotactic coordinates: AP+1.7; LAT–0.3; Depth–0.4). Animals were sacrificed three days later. Brains were then processed, stained for β-galactosidase activity and counterstained with neutral red as described in the preceding figures.

Figure 4A:
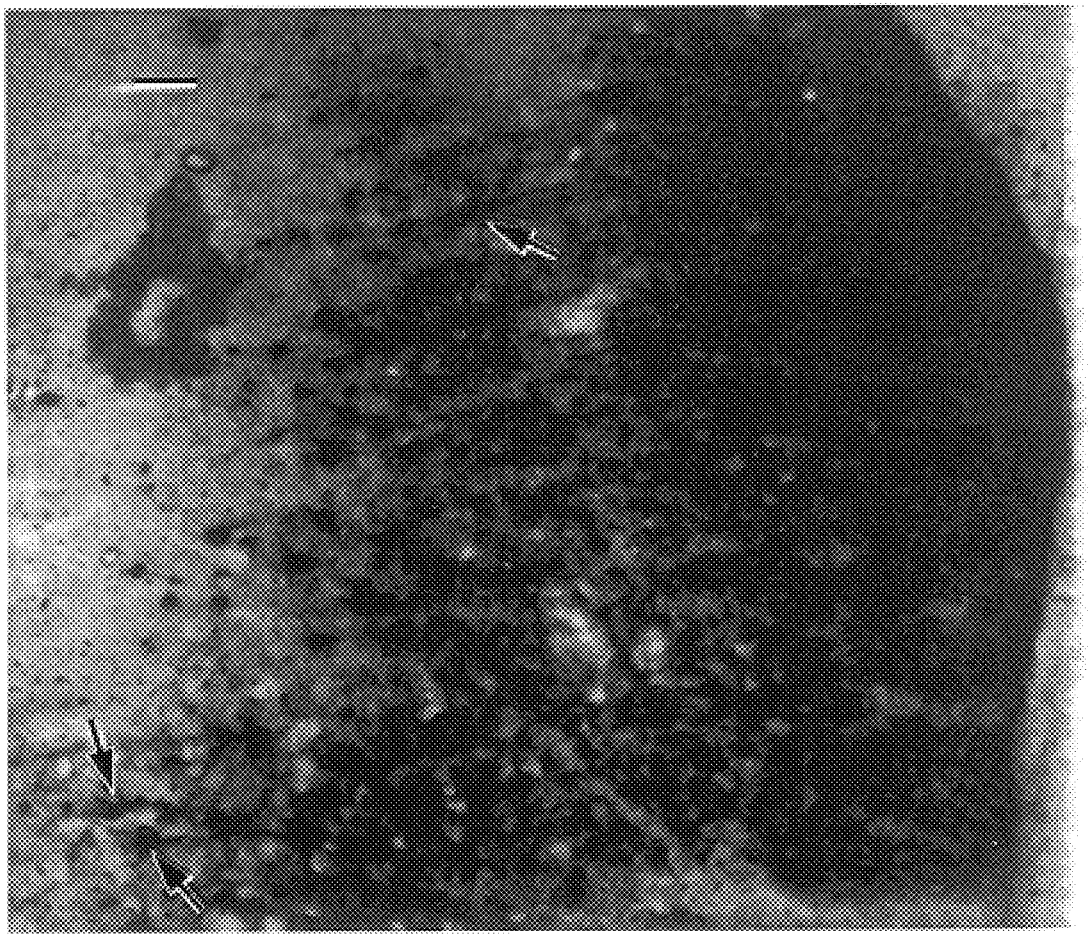
FIG. 4 shows 7134-mediated β-galactosidase gene expression in (a) cerebral cortex, and (b) pyramidal neurons in cerebral cortex.
Figure 4B:

In some rats expression of the lacZ gene was evident in a relatively large area of the cingulate cortex (FIG. 4a), probably due to retrograde transport of the virus from the caudate. Examination of the cingulate cortex at higher magnification revealed discrete labeling of pyramidal neurons, identified by characteristic morphology (FIG. 4b). Reaction product was apparent throughout dendrites and axons. Most of these neurons did not show evidence of degeneration, such as swelling or beading of processes. It was also evident β-galactosidase gene expression was not as apparent in non-neuronal cell types.

In these studies, lacZ gene transfer and expression into CNS neurons was achieved using replication deficient HSV-1 mutants. The majority of cells expressing lacZ following inoculation of the 7134 replication-compromised mutant possessed the morphological characteristics of neurons. In addition, many of the neurons expressing lacZ (following caudate inoculation) were found some distance away in the cingulate cortex, raising the possibility that the virus possesses a particular trophism for this cortical region. This finding also supports the occurrence of retrograde transport of the mutant virus following from nerve endings in the caudate to cell bodies in the cortex. Transneuronal transport can deliver genes to specific neurons via inoculation into areas containing their axonal or dendritic projections. Recent findings using wild type HSV-1 indicate that transneuronal and transsynaptic transfer can be followed using $^3$H-thymidine labeling and immunocytochemical staining of viral antigens. (Ugolini et al., *Science* 243:89 (1989); Norgren, Jr. et al., *Brain Res.* 479:374–378 (1989); Margolis et al., *J. Virol.* 63:4756–4761 (1989); Kuypers et al., *TINS* 13:71–75 (1990).) The viral vectors with the lacZ substitutions thus should be used for transsynaptic transport. This provides a useful tool to neuroanatomically trace specific neuronal projections and synaptic pathways with less toxicity to animals.

TABLE 1

Survival of Rats After Intercerebral Injection of Virus

| Mutant | Days After Injection | | |
|---|---|---|---|
| | 1 | 3 | 14 |
| Control[a] | 12/12[b] | 8/8 | 4/4 |
| 7134 | 26/26 | 8/8 | 6/7[c] |
| 7134 | 12/12 | 12/12 | 12/12 |
| GAL4 | 15/15 | 11/11 | 3/3 |
| RH105 | 12/12 | 8/8 | 4/4 |
| KOS | 19/19 | 15/15 | 1/8[d] |

[a]Equal volume of medium was injected.
[b]Expressed as animals surviving/animals inoculated on day 0.
[c]Death of one animal occurred 8 days after injection. This animal exhibited lethargy and inactivity prior to death.
[d]Animal deaths occurred 6–7 days after inoculation and were preceded by frequent seizures 5 days following inoculation.

Example 3
Materials and Methods
Plasmid Construction

A 3.2 kb fragment from plasmid pBRTK, (Colbere-Garapin et al., *Proc. Natl. Acad. Sci. USA* 76:3755–3760 (1979)), containing the entire HSV-1 thymidine kinase gene was ligated into the BamHI site of p19 plasmid to remove additional H-3 sequences. The HSV-tk gene was then cleaved with Sac I and ligated with a 1.8 kb Sac I fragment containing the rat NSE promoter. A 4.0 kb H3 DNA fragment containing the bacterial lacZ gene followed by 3' regulatory sequences from the human enkephelin gene was ligated into the H3 site of the polylinker at the 3' end of the NSE promoter to form a pNSE-lacZ-TK cassette at the Sac I site of the HSV-tk gene. The resulting plasmid was confirmed by restriction analysis.

Construction of Recombinant pNSE-lacZ Containing-HSV-1 Virus

Cotransfection was carried out as previously described with 10 micrograms of Bg1 II linearized pNSE-lacZ-TK plasmid DNA and 2 micrograms of KOS HSV-1 DNA into 100 mm$^2$ plates of Vero cells grown in 10×1 media (Dulbecco's modified Eagle's media (Gibco) containing 10% fetal calf serum (FBS, Gibco), 100 units/ml of penicillin, 100 micrograms/ml of streptomycin, and 7.5% bicarbonate) (Javier et al., *J. Virol.* 62:1381–1387 (1988)). After extensive cytopathic effects were observed (5–7 days at 37° C.), media containing virus and cellular debris were collected and centrifuged 10 minutes at 4° C. in a table-top centrifuge to remove unlysed cells. The resulting supernatant was centrifuged for 60 minutes, 4° C., in a SA600 rotor at 9000×rpm to pellet the virus. The viral pellet was combined with the unlysed cellular pellet (kept on ice) in 1.0 ml of 10×1 media. This was freeze-thawed 3× at –70° C. to lyse the cells, spun 5 minutes at 4° C. in a table-top centrifuge to remove lysed cells, and the resulting viral supernatant stock stored at –70° C. in 15% glycerol.

The viral stock was diluted $10^3$, $10^5$, and $10^7$ in 10×1 media and 100 microliters of each dilution plated onto confluent 100 mm$^2$ plates of Vero cells grown in either 10×1 media alone, or media containing 133 micromolar acyclovir. These were incubated for 60 minutes, 37° C. with occasional rocking, then overlaid with 0.7% agarose±133 micromolar acyclovir.

After 5 days, individual "cloudy" plaques were isolated from the infected Vero plates grown in the presence of acyclovir and transferred by sterile pasteur pipets into 0.5 ml of 10×1 media. These were freeze-thawed at –70° C. 3×, then stored at –70° C. in 15% glycerol.

Virus from the acyclovir-resistant plaque stocks was amplified for DNA isolation by addition of 250 microliters of each individual stock into 1 ml of 10×1 media containing $10^5$ Vero cells, and growing for 2–3 days until cytopathic effects were evident. The cultures were then vortexed and frozen at –70° C. These were used for viral minipreps.

Approximately 1.0 ml of each amplified viral stock was transferred individually to a microfuge tube and microfuged for 60 minutes at 4° C. The resulting pellets were washed with 0.5 ml of PBS and microfuged for 10 minutes, 4° C. to pellet. The pellets were then resuspended in 180 microliters of PBS, 10 microliters of 10% SDS, and 5 microliters of 20 milligrams/ml proteinase K and incubated for 4 hrs. at 37° C. Phenol extraction was performed on the samples, followed by a 1:1 phenol:chloroform extraction, and a chloroform extraction. DNA was EtOH precipitated in the presence of 0.3 M Na Acetate, pH 5.2 at –70° C. for 5 minutes and pelleted 10 minutes, 4° C. in a microfuge. The pellets were washed in 70% EtOH and air-dried; the DNA was resuspended in 30 microliters TE.

One microliter of DNA from each acyclovir-resistant viral isolate was transferred onto nylon membrane (Hybond) and air-dried. The dot blot was denatured 5 minutes in 1.5 M NaCl, 0.5 M NaOH, followed by neutralization for 8 minutes in 1.5 M NaCl, 0.5 M Tris-HCl, pH 7.5, and then rinsed in 3×SSC (1×SSC=0.15 M NaCl, 0.015 M sodium citrate). The blot was baked at 80° C. for 2 hrs, pre-washed in 0.5% SDS and 0.1×SSC for 1 hr. at 65° C., and hybridized as described (see, Maniatis et al., *Molecular Cloning: A Laboratory Manual*, Cold Spring Harbor Press, USA (1989) and the references cited therein) with a β-galactosidase probe to look for the presence of lacZ in the viral construct. The probe used was the 4.0 kb $H_3$ lacZ-ENK fragment and was prepared by $^{32}$P labelling by the random primer method (Boehringer Mannheim kit). Viruses that gave a positive signal were tested for the presence of the pNSE-lacZ-TK cassette by PCR analysis using primers that define an amplification target fragment of 900 base pairs extending across the 3' region of the NSE promoter to the middle of the lacZ coding region (primer+primer).

The PCR reactions were carried out per the manufacturer's directions (ProMega), using 1 microliter of DNA from each lacZ positive virus and 15 micromoles of each primer. DNA was denatured for 5 minutes at 94° C. prior to starting the PCR reaction. The cycling conditions were denaturing at 94° C. for 1 minute, annealing at 55° C. for 2 minutes, and extension at 72° C. for 3 minutes for 25 cycles. Linearized pNSE-lacZ-TK was run as a positive control. The resulting PCR products were separated on a 1% agarose gel, stained with EtBr, and photographed under UV light. The gel was analyzed by Southern blot hybridization (Southern, E., *Meth. Enzymol.* 68:152–176 (1979)) using a β-galactosidase probe to ensure the resulting 900 base pair band was derived from amplification of the pNSE-lacZ-TK cassette.

Virus containing the pNSE-lacZ-TK cassette was amplified to a titer of 5×10$^8$ PFU/ml and stored at –70° C. in 15% glycerol. Retitering of the viral NSE-lacZ-TK viral stock after repeated freeze-thawing revealed no decrease in titer. Titer was determined by infecting Vero cells with various dilutions of the stock virus and determining the number of PFU per volume.

Cell Culture and Viral Infections

All cell lines were grown in 6 or 12 well dishes in DMEM containing 10% FCS, 100 units/ml penicillin, and 100 micrograms/ml streptomycin (D-10), with the exception of the dorsal root ganglion (DRG) cells, (Baccaglini et al., Proc. Natl. Acad. Sci. USA 20:594–498 (1983)) and grown in D10 with the addition of 10 ng/ml NGF and the Vero cells that were grown in 10×1 media. RH116 virus (Mokorski, Virology 167:279–283 (1988)) contains the early viral gene promoter, β-8 driving lacZ expression from the HSV-tk site, and was used as a positive control for expression of β-galactosidase in all cell culture experiments described here. Negative controls consisted of cells infected with media alone. For most cell types, media were removed and the cells were infected at MOIs of 10, 1, 0.1, and 0.001 with approximately 100 microliters of either NSE-lacZ-TK or RH116 virus, or the same volume of media alone, incubated for 1 hr. at 37° C., and the infected cells were overlaid with 0.7% agarose. Veros were infected at a viral titer of 100 PFU/plate with various viruses. After 2–3 days, the cells were examined under the light microscope for the presence of plaques and then stained with X-gal overnight at 37° C. (X-gal solution contains 1.0 mg/ml 5-bromo-4-chloro-3-indolyl-β-D-galactosidase (X-gal), 5 mM potassium ferricyanide, 5 mM potassium ferrocyanide, and 2 mM magnesium chloride in PBS). For the DRG cells, media were not removed but rather the cells were infected by addition of virus directly to the media. After 3 days, media were removed and the cells were fixed with cold EtOH, rinsed with PBS, and stained with X-gal as above. The next day, the number of histochemically stained cells or plaques were examined under a light microscope.

N1E115TG2 cells were lipofected with the pNSE-lacZ-TK plasmid according to the manufacturer's (BRL) directions overnight at 37° C., fixed with 0.5% glutaraldehyde, and stained with X-gal as above.

Intracerebral Inoculation of Animals

Approximately $1 \times 10^6$ PFU of NSE-lacZ-TK virus was injected into the right frontal brains of 151–175 g Fisher adult male rats with the aid of a stereotactic device (coordinates=AP+0.17, LAP–0.31, depth–0.4 from Bregma, where the coronal and sagittal sutures cross) in a volume of 10 microliters with a Hamilton syringe. The rats were anesthetized with 1.5 ml of Rat Nap (16.2% nembutal, 10% ethanol, 39.6% polyethylene glycol, 166 mM magnesium sulfate, and 4.25% chloral hydrate). A skin incision was made to expose the top of the skull, a small hole was drilled into the skull at the specified coordinates to allow entry of the syringe into the frontal cortex, the virus was injected over a period of 3 minutes by slow pressure, and the wound was closed with surgical clips. Three animals were injected per time point with either virus or with media alone as control. Rats were monitored daily for abnormal behavior or seizures. Three or 14 days post injection, animals were anesthetized and sacrificed by intracardiac perfusion with 200 ml of PBS, pH 7.4. The tissue was fixed by intracardiac perfusion with 200 ml PBS containing 4% paraformaldehyde. Brains were removed and fixed overnight at 4° C. in the same fixative. The brains were then processed over 3 days by placing them serially in increasing concentrations of sucrose in PBS (15%, 20%, and 30%) for 24 hrs. at 4° C. Brains were then frozen on dry ice and sectioned coronally on a cryostat in 30 micron sections. These were washed with PBS and placed overnight in 0.01% X-gal solution containing 0.02% Nonidet P-40 and 0.01% sodium deoxycholate at 37° C. The stained sections were then rinsed with PBS, mounted on glass slides, air-dried, counterstained with hematoxylin (HNE), coverslipped with Permount, and examined by light microscopy for blue product indicating the presence of β-galactosidase activity.

Results

Figure 5:
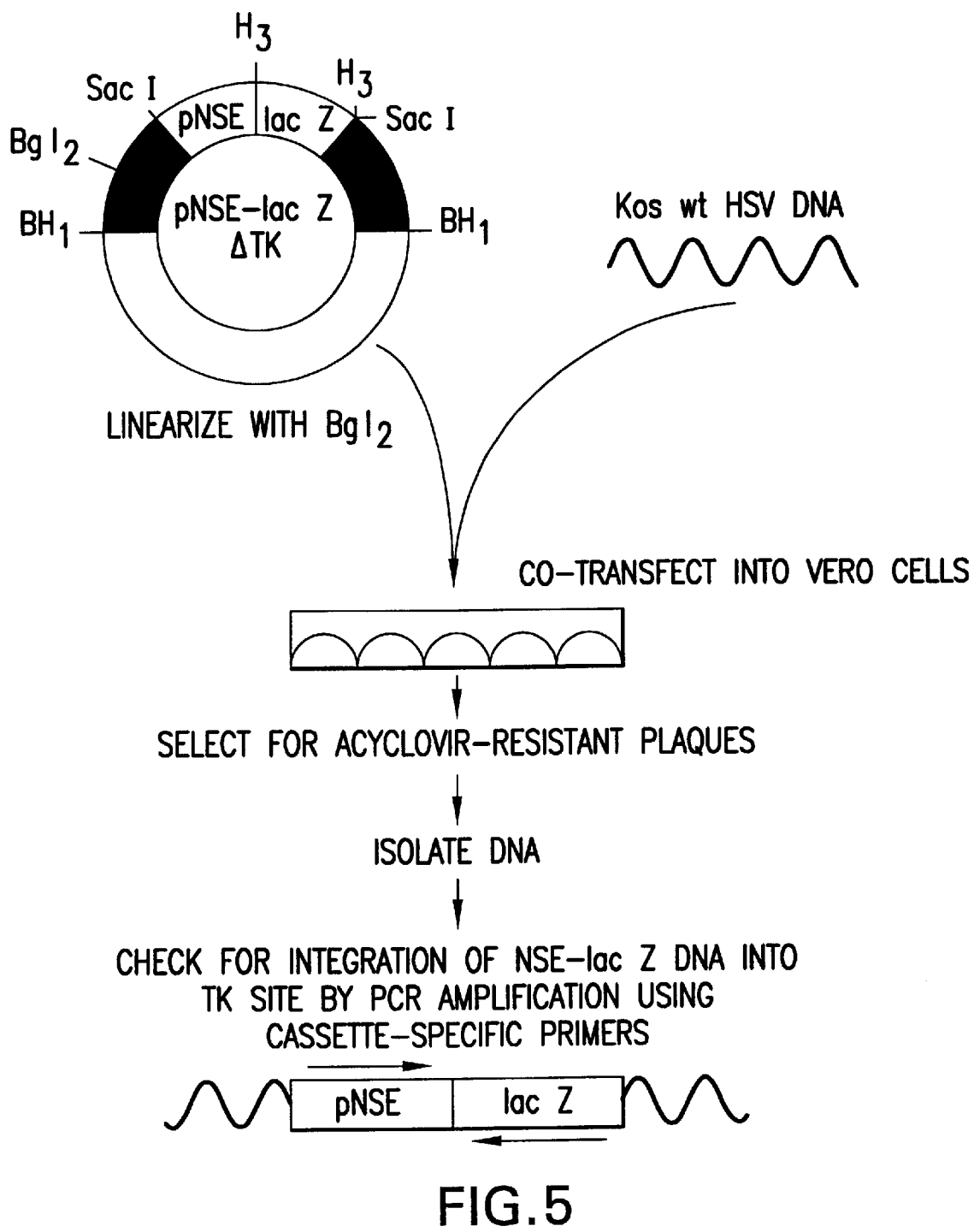
FIG. 5 shows a general outline for construction of recombinant NSE-lacZ-TK virus. Refer to Materials and Methods section for specific details of experimental protocols used.

A bacterial lacZ marker gene under control of the rat NSE promoter was introduced into the HSV-1 viral genome by DNA-mediated marker rescue (Smiley, Nature 285:333–335 (1980)). As shown in FIG. 5, first the pNSE-lacZ-TK cassette was introduced into the Sac I site of a 3.2 kb DNA fragment containing the HSV-tk gene cloned into the E. coli plasmid p19 (a puc derivative). The Sac I site was chosen as the site for integration because it had been previously shown by others that disruption of this site will render the resulting virus deficient for HSV-thymidine kinase activity, thus allowing for its selection with acyclovir or other toxic nucleoside analogue drugs (Coen et al., Proc. Natl. Acad. Sci. USA 86:4736–4740 (1989)). Also, integration of the cassette at this site leaves greater than 500 base pairs of homologous HSV-tk sequence on either side of the pNSE-lacZ-TK fragment; this amount is the minimum amount of TK sequence that is needed for recombination to occur between the TK sequences of the recombinant plasmid and HSV-1 viral DNA (Breakefield and DeLuca, New Biologist 3:203–218 (1991)).

The plasmid was linearized and co-transfected with wild-type KOS HSV-1 DNA into Vero cells by calcium phosphate precipitation (See, Javier et al., supra (1988)). After a few days, virus was harvested from the transfection and used to infect Vero cells in the presence or absence of acyclovir. This was done: (1) to estimate the frequency of recombination between the pNSE-lacZ-TK plasmid and HSV-1 viral DNA and (2) to allow for isolation of acyclovir-resistant plaques. Comparing the titer of acyclovir-resistant plaques to the titer of total plaques formed per a given volume of virus reveals a recombination frequency of about $1:10^4$, well within the range expected.

Figure 6:
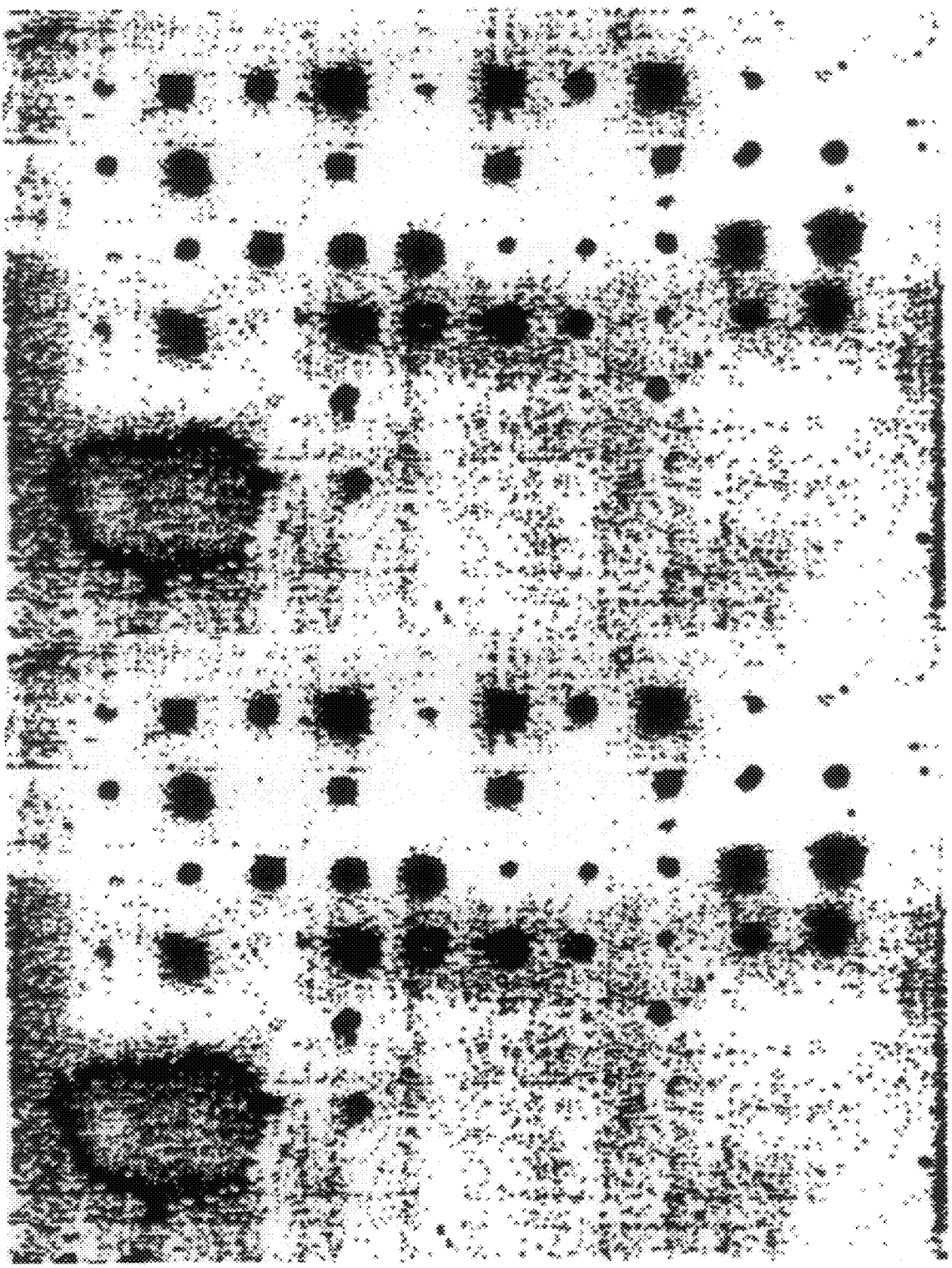
FIG. 6 shows a dot hybridization of DNA isolated from a recombinant acyclovir-resistant HSV plaques with $^{32}$P-labeled lacZ probe. DNA from 49 amplified acyclovir-resistant viral plaque stocks was isolated as described, "dotted" sequentially onto duplicate grids, and probed with 32P-labeled lacZ gene fragment. Those given a positive signal were selected for further analysis. The two dots in the lower left-hand corner represent pNSE-lacZΔTK plasma as a positive control.
Figure 7:
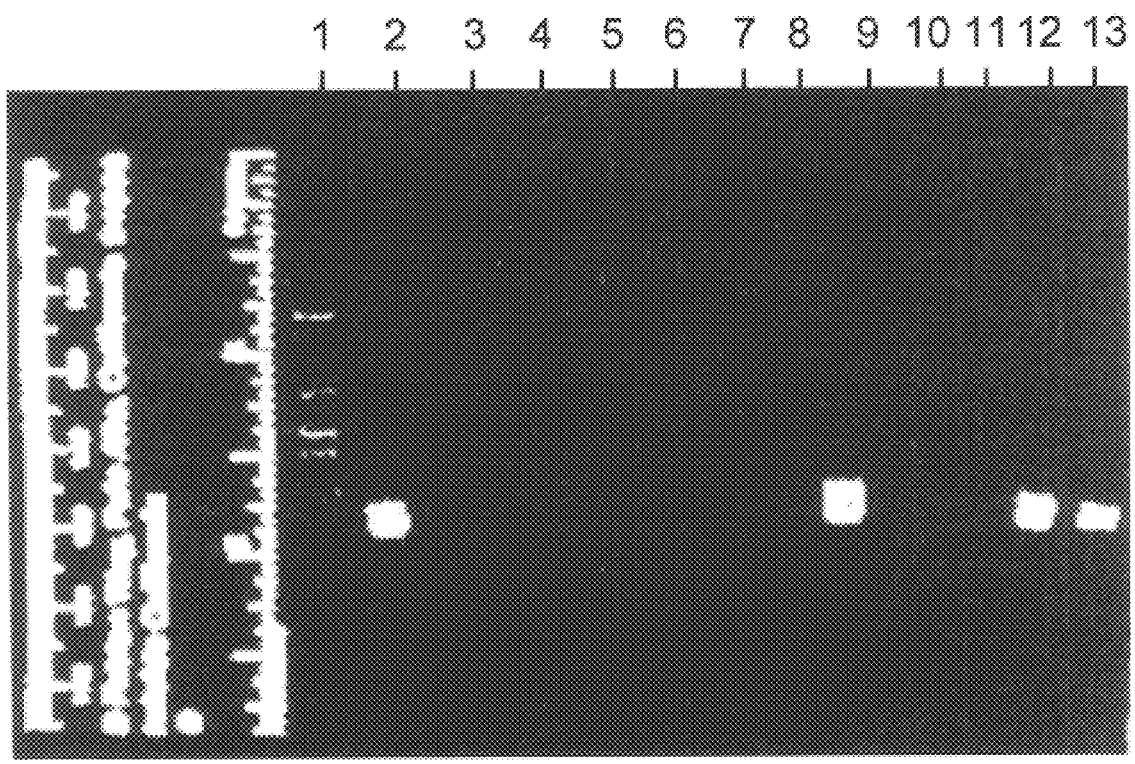
FIG. 7 shows a classification of HSV recombinants containing the NSE-lacZ-TK cassette by PCR analysis of DNA isolated from acyclovir-resistant plaques. Lanes 3–13 represent DNA isolated from 11 acyclovir-resistant plaques, three of which (9, 12, 13) were identified as positive for the presence of the integrated NSE-lacZ-TK cassette by the presence of a 900 bp fragment. Lane 2 represents NSE-lacZΔTK plasmid as a positive control, and lane 1 corresponds to DNA site markers.
Figure 8:
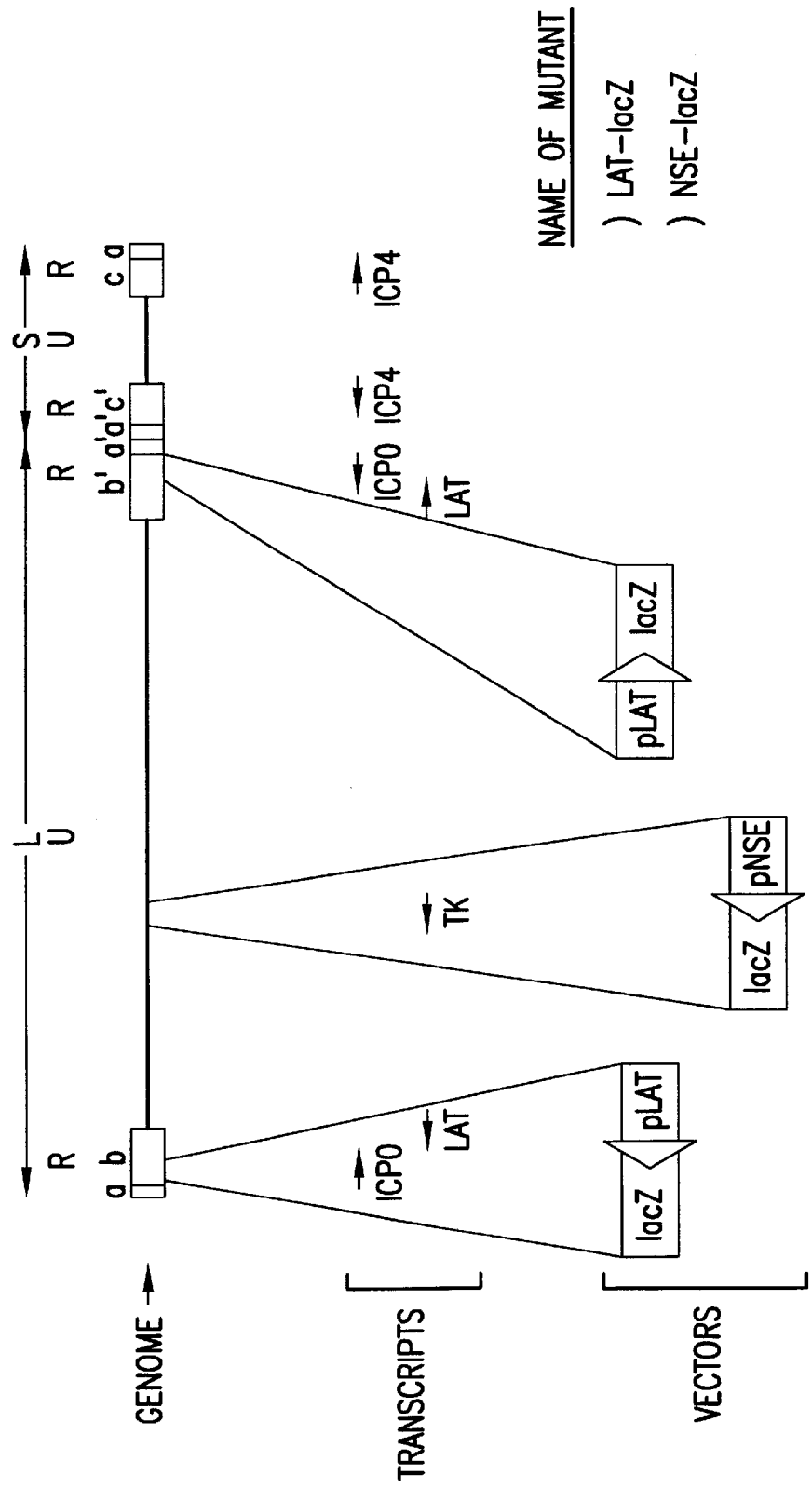
FIG. 8 shows a scheme of HSV constructs using either the LAT promoter or the NSE promoter to drive foreign gene expression in neurons. Note that NSE-lacZ-TK requires integration of the appropriate cassette into a single site in the long unique region of the HSV genome, while for plat-lacZ, integration at both lat sites in the HSV short repeat region is necessary.

Acyclovir-resistant plaques were isolated and DNA prepared to look for the presence of the pNSE-lacZ-TK cassette in these viruses. Aliquots of DNA prepared from amplified acyclovir-resistant viral stocks were dotted onto duplicate membranes and probed with a $^{32}$P-labeled bacterial β-galactosidase probe (FIG. 6). Those testing positive for the presence of lacZ were further analyzed by PCR amplification to look for the presence of a 900 base pair target fragment extending across the integrated pNSE-lacZ-TK cassette (FIG. 7). The presence of pNSE-lacZ-TK within the HSV-tk gene was further verified by Southern analysis of the PCR gel probed with the β-galactosidase probe (data not shown). Of the 50 initial acyclovir-resistant plaques isolated, 14 proved to contain NSE-lacZ-TK by dot-blot hybridization, PCR amplification, and Southern analysis. The remaining acyclovir-resistant plaques are assumed to be the result of spontaneous HSV-tk mutations due to the high error rate of the HSV DNA polymerase causing random incorporation of incorrect bases at the TK locus. One of the NSE-lacZ-TK positive HSV recombinants were grown to high titer ($5 \times 10^8$ PFU/ml) for use as viral stock. When analyzed by plaque hybridization using the lacZ probe, all plaques present were positive, indicating the stock is a pure population of NSE-lacZ-TK virus. A diagram depicting the resulting virus including the pNSE-lacZ-TK integration site is shown in FIG. 8.

To determine whether the NSE promoter in the context of a herpes viral vector will retain its ability to selectively express foreign DNA only in neurons, the NSE-lacZ-TK recombinant virus was used to infect several different cell types in culture, including both primary and continuous cell lines (Table 2).

TABLE 2

Testing of Cell Lines for β-Gal Activity
3 Days Post-NSE-lacZ-TK Viral Infection

| | | | β-gal positive | |
|---|---|---|---|---|
| cell | type | species | RH116 | NSE-lacZ-TK |
| PC12 | adrenal medulla | rat | + | − |
| C6 | glioma | rat | + | − |
| 9L | glioma | rat | + | − |
| 6H4CL | pituitary | rat | + | − |
| N1E115 TG2 | neuroblastoma | mouse | + | + |
| DRG | neuron | rat | + | +(14d = +) |
| — | astrocytes | rat | + | − |
| Veros | kidney | monkey | + | − |

Although cells derived from several different sources were examined, only the neuronal cell types infected with the NSE-lacZ-TK virus showed darkly-stained β-galactosidase (β-gal) positive cells after 2–3 days of infection. In contrast, all cell types infected with RH116, a virus containing an early viral gene promoter, were found to yield β-gal positive cells. For example, when 9L, a rat glioma, or undifferentiated PC12 cells, a rat adrenal medullary line, are infected with either NSE-lacZ-TK or RH116, only RH116 shows β-gal positive cells. In contrast, when a mouse neuroblastoma, N1E115TG2, is infected with either of these two viruses, both show cells stained positively for β-gal expression, although the NSE-lacZ-TK virus gives fewer and less darkly stained cells than seen for infection with RH116 at comparable MOIs. In fact, the number of β-gal positive cells produced by infection with NSE-lacZ-TK is comparable to that produced by RH116 infection at a 10-fold lower MOI, indicating that roughly ten-fold more of the cells infected with RH116 give positive histochemical staining when infected with the same amount of virus. This is probably due to the differing strengths of the two promoters during productive infection, as the RH116 and NSE-lacZ-TK viral constructs only differ in what promoter element they contain.

Note that at high MOIs, even in those cells showing no positive staining after infection with NSE-lacZ-TK, one sees an increase in cytopathic effects.

Similar staining patterns are seen for N1E115TG2 cells transfected with the NSE-lacZ-TK plasmid as for the same cells infected with the NSE-lacZ-TK virus.

Several HSV-1 recombinants containing a bacterial lacZ gene driven by a viral promoter at the HSV-TK site were examined for their ability to give β-gal positive viral plaques when plated on Vero cells; all the viral promoters examined were positive for lacZ expression in contrast to NSE-lacZ-TK virus, which was not.

Rat DRGs fixed and stained with X-gal 14 days post-infection with the NSE-lacZ-TK virus continue to show cells giving β-gal positive staining. In contrast, RH116, while giving many positive cells at 3 days post-infection, shows none by 14 days.

In rat CNS injected with the NSE-lacZ-TK virus, both at 3 days and at 14 days post-infection, β-gal activity was detected by histochemical staining of frozen brain sections. Additionally, β-gal activity was detected in some neurons out to 30 days post-infection. A large number of cells expressing β-gal were present near the site of injection, although many of these are difficult to identify due to the extensive degree of focal tissue necrosis. This necrosis may be due either to the virus itself, or to the large volume of fluid injected into the area, or possibly both. Many pathologic neurons and macrophages are present.

Both diffuse cytoplasmic and "speckled" staining of cells were observed; this agrees with the staining patterns seen by Dobson et al. for their MMLV promoter-driven HSV-1 construct when it was used to infect primary sensory neurons of the lumbar dorsal root ganglion (Dobson et al., *J. Virol.* 63:353–360 (1990)).

Figure 9:
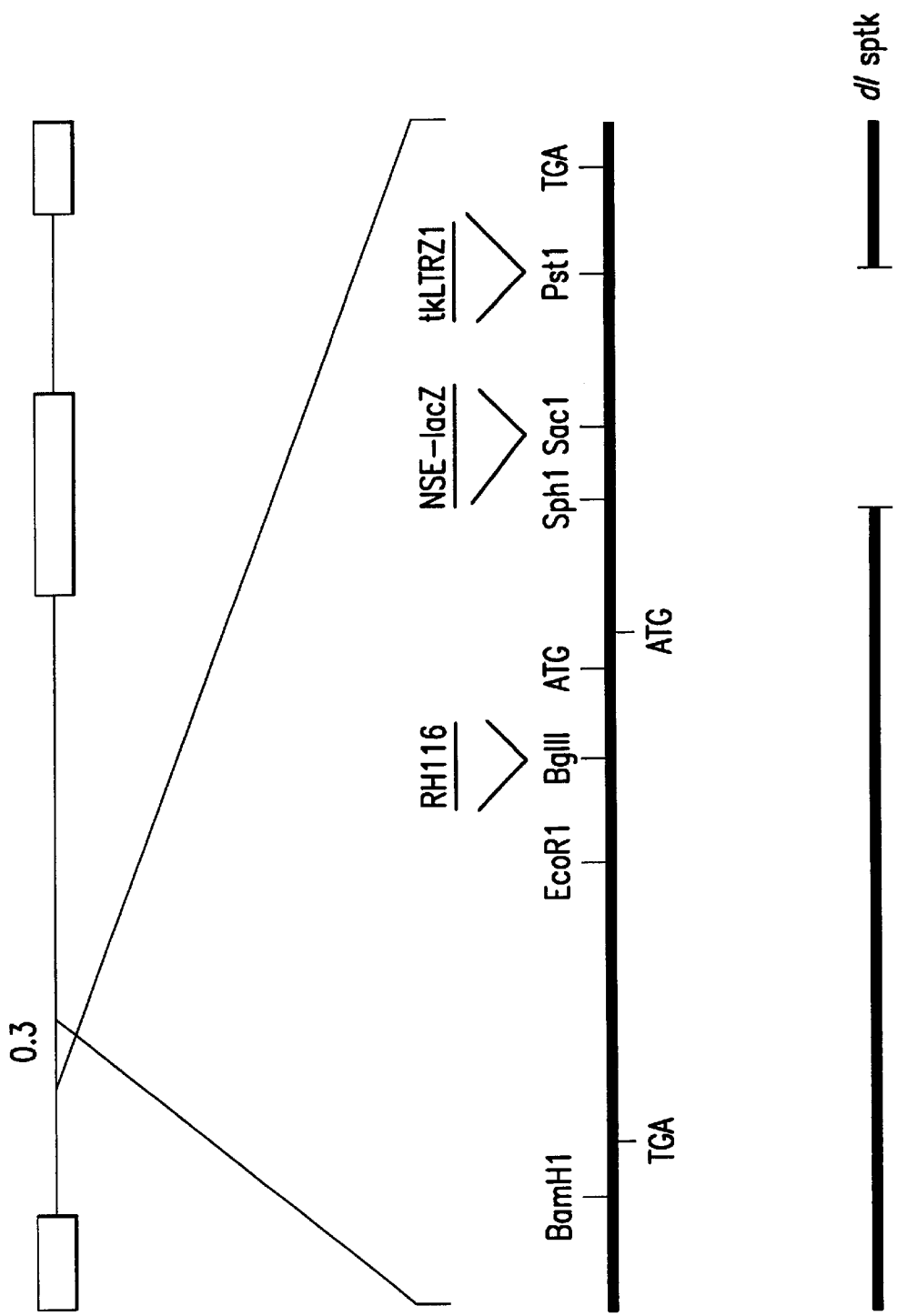
FIG. 9 illustrates the diagram of the herpes simplex virus (HSV) genome. (Upper) The location of the thymidine kinase (TK) gene at map coordinate 0.3 is shown. Long diagonal lines connect to an expanded view of the 3.6 kb BamHI Q fragment encompassing the TK coding region and upstream regions with selected restriction endonuclease sites indicated. Short diagonal lines indicate the locations of the insertion mutations within (vectors NSE-lacZ and tkLTRZ1) and outside (vector RH116) the TK protein coding region. The ATG and TGA marked above the line represent the initiation and termination codons of the TK coding region; the ATG and TGA marked below the line represent the initiation and termination codons of the adjacent UL24 coding region. (Lower) The location of the deletion mutation in mutant dlsptk is shown.

Labeling of cells was more limited outside of the necrotic zone in both 3 and 14 day post-infection brains (about 20 neurons in five sections; FIG. 9), but these cells were clearly identifiable as neostriatal neurons by their size (10–20 microns) and morphology (round/pyramidal cell bodies with some clearly visible labeled axons), and were healthier than the cells seen in the necrotic region. Cell structure would be more visible using β-gal Abs. Brains injected with media alone showed no positive histochemical staining. There was no evidence for either retrograde or anterograde transport in virally infected brains. The spread of positive neurons beyond the necrotic zone with this replication-defective virus may be due to replication in non-neuronal cells in the brain (in endogenous non-neuronal cells or entering immunological cells) or due to traveling microglial cells.

Interestingly, when virus was injected accidently into the lateral ventricle, at three days post-infection, cells within the ependymal region lining the ventricle and endothelial cells lining blood vessels within the brain appear to be β-gal positive; this would indicate that during productive infection, the specificity of activity of the NSE promoter may be over-ridden by immediate-early or early viral proteins. This is not all that surprising, for example, the mouse β-globin gene is also expressed aberrantly during productive viral infection when transduced into cultured cells by a HSV-1 recombinant vector; it appears to give similar expression patterns to early viral promoters (Smiley, Virology 64:3882–3384 (1990)). Also, there is some indication that immediate-early viral proteins will activate any promoter present in the HSV-1 genome that contains a TATA box during lytic infection; the NSE promoter has a modified TATA-like box in its 5' upstream region that may act like a TATA box in this instance (Sakimura et al., *Gene* 60:103–113 (1987)). The behavior of promoters may differ during productive infection vs. latency, as the neuronal specificity of the NSE promoter is apparently maintained at longer times post-infection.

Discussion

One of the important issues in the potential use of HSV-1 vectors for in vivo gene delivery is what promoters can be used to obtain long-term gene expression and where these can be placed in the viral genome. In this study, the ability of a herpes-derived vector containing the mammalian cell-specific NSE promoter placed at the HSV TK locus to drive expression of a foreign gene product, β-galactosidase, both transiently and stably in culture and in the CNS has been analyzed.

In culture, the only cell types that showed β-gal activity at short times post-infection with the NSE-lacZ-TK virus were those of neuronal origin, indicating that the promoter-specificity of NSE was maintained during productive infection in these cells. In addition, primary DRG cells examined 14 days post-infection show continued expression of β-gal activity, at a time when early viral gene promoters are no longer active, indicating there is long-term expression of lacZ from this promoter presumably during latency in tissue culture.

In vivo, β-gal positive cells are seen for extended periods of time (out to 30 days) post-infection in the mammalian CNS. Early on (3 days) post, infection, the types of cells showing β-gal positive expression are not confined to neuronal populations, but this pattern seems to differ with what one sees during long-term expression.

To assure that the long-term expression with the NSE-lacZ-TK viral vector is due to the virus entering latency within the neurons, the infected cells can be examined by in situ hybridization with lat transcript probes to look for the expression of lat transcript expressed during latency. (See, Wagner et al., *J. Virol.* 62:1194–1202 (1988)).

Herpes-mediated cytotoxicity is believed to be due, in large part, to both: (1) viral replication or (2) shut-down of host cellular functions in large part by viral proteins such as UL41 (Smikert and Smiley, *J. Virol.* 64:3882–3894 (1990)), which acts by degrading cellular RNAs, thus reducing translation of host cell transcripts. Because the NSE-lacZ-TK virus is TK deficient, it cannot replicate in post-mitotic cells such as neurons and its toxicity will be reduced in those cells. To eliminate toxicity due to shut-down of host cell functions, the pNSE—lacZ cassette could be placed in the HSV-tk gene of a virus backbone deficient in UL41 (Smiley et al., *J. Virol.* 61:2368–2377 (1987)). Cytotoxicity in culture can be further reduced by use of low MOIs (low MOI appears to drive virus towards latency as opposed to lytic infection) and by reducing viral replication with drugs such as acyclovir genetic manipulation to eliminate genes such as UL41 that are involved in host function shut-down (UL41 is a cellular transcript specific RNAse).

This disclosure represents the first report of long-term expression of a foreign gene under the control of a mammalian promoter with a viral vector. Such long-term expression of a foreign gene under the control of a tissue-specific mammalian promoter indicates both in culture and in vivo that such a construct could be used: (1) to alter neuronal physiology by placing biologically active foreign genes behind the tissue-specific promoters, (2) as a model for defining neuronal-specific promoters in vivo, (3) to define neuronal specific cell types able to enter latency, (4) in neuroanatomical tracing studies, and (5) to introduce genes into neuronal cells in culture.

TABLE 3

TK CONSTRUCTS

| Promoter | | Foreign Gene | Name | Reference |
|---|---|---|---|---|
| HSV | | | | |
| immediate early | pICP4 | lacZ | RH105 | Ho & Mocarski |
| early: | pβ-8 | lacZ | RH116 | Ho & Mocarski |
| late: | pgE | lacZ | VgE2b | Weir |
| non-herpes | | | | |
| constitutive: | pMMLV | lacZ | tklTR | Coen |
| | pRSV | lacZ, ENK | lacZ, ENK | Meaney & Breakefield |
| cell-specific: | pNSE | lacZ | NSE-lacZ | Anderson & Breakefield |
| inducible: | plat | lacZ | tklatZ | Coen |
| | pENK-Cre-7 | lacZ | T7LZ & T7EM | Meaney & Breakefield |

Example 4

In this example, TK⁻ herpes virus vectors, were used to deliver the marker gene, lacZ, to mouse trigeminal ganglion neurons in vivo. The expression of lacZ by these vectors was under the control of different viral or mammalian promoters. The strength of these promoters and their ability to confer stable expression of lacZ on trigeminal ganglion neurons was compared. It was hypothesized that the distribution of histochemical labelling of neurons with these TK⁻ vectors, and possibly the distribution of latency-associated transcripts (LATs) in trigeminal ganglion, would resemble the distribution of neurons innervating the site of inoculation as determined using the retrograde tracer Fluoro-Gold.

To achieve gene delivery to sensory neurons of the trigeminal ganglion, replication-defective, thymidine kinase-negative (TK⁻), herpes simplex viruses (HSV) containing lacZ (the *E. coli* beta-galactosidase gene lacZ) downstream of viral (in vectors RH116 and tkLTRZ1) or mammalian (in vectors NSE-lacZ-TK) promoters were inoculated onto mouse cornea and snout.

Trigeminal ganglia were removed at 4, 14, 30 or 60 days after inoculation with vectors and histochemically processed with 5-bromo-4-chloro-3 indolyl-beta-galactoside (X-Gal). With vector tkLTRZ1, large numbers of labeled neurons were observed in rostromedial and central trigeminal ganglion at 4 days after inoculation. A gradual decline in the number of labeled neurons was observed with this vector at subsequent time points. With vectors RH116 and NSE-lacZ-TK, smaller numbers of labeled neurons were seen at 4 days following inoculation than were observed with vector tkLTRZ1. No labeled neurons could be observed at 14 days after inoculation with vectors RH116 and NSE-lacZ-TK.

Immunocytochemistry for *E. coli* β-galactosidase and in situ hybridization to HSV latency-associated transcripts revealed labeled neurons in regions of the trigeminal ganglion similar to that observed with X-Gal staining. A comparable distribution of labeled neurons in trigeminal ganglion was also observed after application of the retrograde tracer Fluoro-Gold to mouse cornea and snout.

These data are evidence that retrogradely transported TK⁻ herpes virus vectors can be used to deliver functional genes to sensory neurons in vivo in an anatomically predictable fashion.

1. Methods a. Viral Vectors

HSV vectors were constructed in a wild type herpes simplex virus type 1 (KOS strain) DNA background (Smith, *Proc. Soc. Exp. Biol. Med.* 115:814–816 (1964)), and were thymidine kinase-negative (TK⁻) due to insertion of foreign elements into, and/or a deletional mutation in the TK site. The following HSV vectors containing lacZ were tested: RH116 (insertional mutant; lacZ downstream of the HSV beta 8 promoter; (Ho et al., *Virology* 167:279–283 (1988)), tkLTRZ1 (insertional mutant; lacZ downstream of the Moloney murine leukemia virus long terminal repeat promoter), and NSE-lacZ-TK (insertional mutant, lacZ downstream of the neuron-specific enolase promoter) (Andersen et al., *Human Gene Therapy* (in press) (1992)) (FIG. 9).

To construct tkLTRZ1, a plasmid (p tkLTRZ1) was generated by subcloning the 3 kb lacZ BglII fragment from pJ3β-gal, into the polylinker 3' to the MoMLV-LTR in pJ4 ω. The 3.4 kb LTR-lacZ fragment from this plasmid was subsequently cloned into the Pst I site in a plasmid containing the TK coding sequences from the BglII side to the PvuII site (Coen et al., *Proc. Natl. Acad. Sci. USA* 86:4736–4740 (1989)) in the same orientation as TK, thus utilizing the TK polyadenylation signals. Recombinant virus was generated by co-transfection of linearized ptkLTRZ1 and HSV-1 (KOS) infectious DNA in Vero cells, selected by acyclovir resistance as previously described (Coen et al.,

*Proc. Natl. Acad. Sci. USA* 86:4736–4740 (1989)), screened by polymerase chain reaction and amplification of the region of the TK gene encompassing the PstI insertion site, and three times plaque purified. Virus was grown and titered on Vero cells, and maintained in DMEM (Gibco) media at −70° C. Details of the construction of NSE-LacZ-TK vector have been described by Andersen et al., *Human Gene Therapy*, (in press) (1992). In addition to these lacZ-containing vectors, the non-lacZ-containing TK$^-$ mutant dlsptk (deletion mutant; (Coen et al., *Proc. Natl. Acad. Sci. USA* 86:4736–4740 (1989)) was also evaluated. All viruses used for inoculation procedures were kept in 15% glycerol or tissue culture media (DMEM (Gibco)) with 10% fetal calf serum, 100 μ/ml penicillin and 100 μ/ml streptomycin at −70° C. prior to use. Titration to obtain an estimate of the number of plaque-forming units per milliliter (PFU/ml) was performed in Vero cells.

b. Inoculation Procedures

Figure 10:
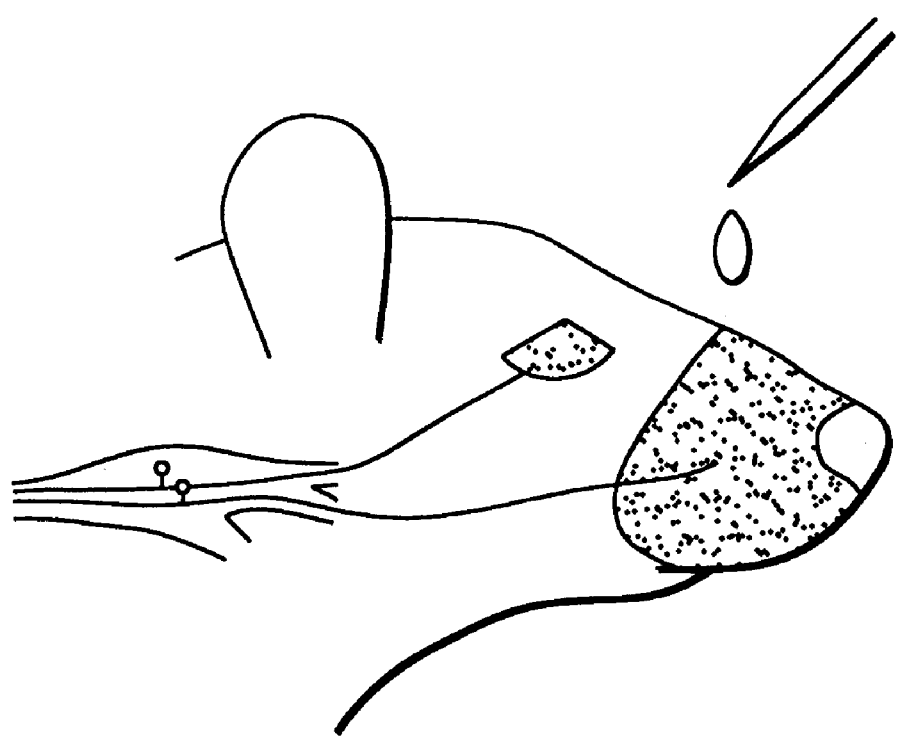
FIG. 10 illustrates mouse cornea and mystacial vibrissal pad, indicating the scarified areas (hatched lines) onto which HSV vectors were inoculated. A sketch of the trigeminal ganglion, the three divisions of the trigeminal nerve, and the peripheral terminations of the first and second divisions of the trigeminal nerve are also shown.

Male Swiss Webster mice 10–16 wks of age (30–50 g) were anesthetized with 0.001 ml/g body weight of a 1:1 solution of ketamine (100 mg/ml) and xylazine (20 mg/ml). The corneal surface was lightly scarified with a 20 gauge needle; the mystacial vibrissae on the same side were clipped and the surface of the vibrissal pad shaved, and then lightly scarified with an emery board or 25 gauge needle. 100 μl of RH116 ($4 \times 10^6$) plaque forming units (PFU)/ml (n=14), tkLTRZ1 ($3.8 \times 10^6$ PFU/ml) (n=26), and NSE-lacZ-TK ($1 \times 10^8$ PFU/ml) (n=12) were inoculated onto these surfaces (FIG. 10). The nasal openings were lightly covered with absorbent toweling in order to prevent the inoculum from reaching the nasal mucosae. Control mice were either inoculated with TK$^-$ vector that did not contain the lacZ gene (100 μl of dlsptk, $3 \times 10^7$ PFU/ml) (n=4) or underwent corneal scarification and snout shaving and scarification without inoculation of vector (n=4). Mice were allowed to recover from the effects of anesthesia and housed individually in covered Nalgene cages in a BL-2 facility under a 12 hr light-day cycle with water and food ad libitum. Observation for signs of illness or infection was performed daily or every other day.

c. Histochemistry

At 4, 14, 30 and 60 days (d) following corneal and snout inoculation with vectors or control procedures, mice were deeply anesthetized with 0.001 ml/g of a 60 mg/ml solution of sodium pentobarbital and then intracardially perfused first with 0.9% normal saline (50 ml) at room temperature followed by 75 ml of 2% paraformaldehyde in 0.1 M phosphate buffer (PB) (pH 7.2–7.4). Both trigeminal ganglia were removed, post-fixed for 1–2 hr in 2% paraformaldehyde (in PB pH 7.2) at 4° C. and then incubated overnight at 37° C. in 1% 5-bromo-4-chloro-3-indolyl-beta-galactosidase (X-Gal) in a solution containing 0.01% sodium deoxycholate, 0.02% Nonidet P-40 (NP-40), 35 mM potassium ferricyanide, 35 mM potassium ferrocyanide and 2 mM magnesium chloride in PB (Price et al., *Proc. Natl. Acad. Sci. USA* 84:156–160 (1987)). Histochemically reacted ganglia were placed in 30% sucrose at 4° C. for 24 hr and then sectioned in the coronal plane at 10–40 μm on a cryostat (Reichert-Jung). Several ganglia were cut in the sagittal plane; these sections were used to calculate a correction factor for neuronal cell counts (Abercrombie, M., *Anat. Rec.* 94:239–247 (1946); Burstein et al., *Brain Res.* 511:329–337 (1990))). Every section was mounted directly onto prepared glass slides (Fisher, Superfrost Plus) and then air-dried at room temperature. Slide-mounted sections were rehydrated in phosphate buffered saline (PBS) for 2 min, dH$_2$O for 1 min, and then transferred to Neutral Red in acetate buffer (pH 4.5) for 3 min and then to dH$_2$O for 30 sec prior to cover-slipping with Crystal Mount (Biodema Inc.).

Permanently mounted sections were examined under brightfield in a light microscope. Trigeminal ganglion tissue was examined for the presence of infection (neuronal cell swelling, chromatolysis, cytoplasmic vacuolation), inflammation (lymphocytic or plasma cell infiltrate), or degeneration of satellite cells (residual nodules of Naegotte) (Mazza et al., *Arch. Oral Biol.* 17:377–387 (1972); Adams et al., *Greenfield's Neuropathology*, New York, John Wiley & Sons, p. 837 (1984); Yamamoto et al., *J. Neurosurg.* 60:108–114 (1984)). Cells positively stained for beta-galactosidase (blue reaction product) were examined for neuronal morphology by comparison with adjacent trigeminal ganglion neurons counterstained with Neutral Red. Criteria for identifying labelled cells as trigeminal ganglion neurons included: a typical rounded or ellipsoid shape, size range 15–50 μm diameter (Sommer et al., *Brain. Res.* 346:310–326 (1985)), a visible neuronal nucleus or nucleolus, and the presence of perineuronal satellite cells. The number of labelled neuronal profiles present in tissue from each animal was counted, and classified according to staining pattern. In one representative case, a reconstruction of the distribution of labelled trigeminal ganglion neurons, observed 4d after inoculation with vector tkLTRZ1, was performed with the assistance of a drawing tube attached to a light microscope. In another experimental animal, 4d after inoculation with vector tkLTRZ1, all labeled neurons in the trigeminal ganglion containing a visible nucleus, were measured in the longitudinal plane to obtain an estimate of cell diameters.

d. Immunocytochemistry

In two additional animals inoculated with vector tkLTRZ1, trigeminal ganglia were analyzed immunocytochemically (using polyclonal rabbit anti-*E. coli* β-galactosidase antibody (5 Prime to 3 Prime, Inc.)) at 4d for the presence of β-galactosidase protein product. After removal of ganglia as above, coronal sections were cut (20 μm), mounted onto prepared slides (Fisher, Superfrost Plus), and kept at −21° C. prior to immunocytochemical processing. Slide-mounted sections were thawed to room temperature, and treated with 0.3% H$_2$O$_2$ and 50% methanol in PB for 20 minutes, followed by 10×3 minutes washes in PB. Sections were then incubated with 10% goat serum in PB for 60 minutes prior to incubation in primary antisera (diluted 1:1000) overnight at room temperature in a humidified chamber. The following day, sections were washed 10×1min in PB, 10×2 min in 5% blocking (goat) serum and then incubated for 60 minutes with secondary antibody (goat anti-rabbit; Vector laboratories, Vectastain kit) in the humidified chamber. Sections were then washed 10×3 min in PB, followed by final incubation in avidin-biotin-peroxidase complex (Vector Laboratories, Vectastain kit) for 60 min. Ten 1 minute washes in PB followed by 10×2 min washes in 0.05 M Tris buffered saline (TBS). The sections were reacted in diaminobenzidine (DAB) (5% in TBS) and 30% H$_2$O$_2$/10 ml DAB solution and then examined by brightfield light microscopy for the presence of beta-galactosidase immunoreactive neurons.

e. In Situ Hybridization

Trigeminal ganglia from both sides were removed, as described above, 6d after corneal and snout inoculation with vector NSE-lacZ-TK. These trigeminal ganglia were post-fixed for an additional 1–2 hr in 2% paraformaldehyde (in PB, pH 7.4), transferred to 30% sucrose in PB at 4° C. overnight and then sectioned in the coronal plane at 10 μm on a cryostat. Sections were mounted directly onto gelatin-coated slides prepared for in situ hybridization according to the method of Stroop et al. (Stroop, W. G., et al., *Lab. Investig.* 51:27–38 (1984)). Hybridization was performed to sectioned tissue as described by Stroop et al.( Stroop, W. G., et al., *Lab. Investig.* 51:27–38 (1984)) using a $^{35}$S-labelled DNA probe (plasmid pIPH) (Leib et al., i J. Virol. 63:2893–2900 (1989)) containing a 1.4 kb fragment from within the latency-associated transcript (LAT) encoding region. This probe does not overlap transcripts of the adjacent immediate early gene (ICPO) (Leib et al., *J. Virol.* 63:2893–2900 (1989)). After hybridization, tissue sections were dehydrated and dipped in Kodak NTB-2 liquid emulsion prior to development. After developing, sections were counterstained with giemsa, coverslipped and examined by brightfield light microscopy for the presence of LAT-positive neurons.

f. Fluoro-Gold Retrograde Tracing

The fluorescent tracer Fluoro-Gold (20 μl of a 4% solution in 0.9% saline) was applied to the scarified cornea and shaved/scarified snout of two animals. The ipsilateral and contralateral trigeminal ganglia were removed, post-fixed in 2% paraformaldehyde in PB, for 1–2 hr, and then placed in 30% sucrose in PB overnight prior to sectioning at 40 μm on a cryostat. Sections were mounted onto gelatin-coated slides and then dehydrated in Xylene for 5 min before being permanently mounted in DPX mounting medium (BDH chemicals). Sections were examined for Fluoro-Gold labelling of neurons using fluorescence microscopy.

g. Cell Counts and Data Analysis

Quantification of labelled neurons was performed for sections reacted with the histochemical substrate X-Gal. Since labelled neurons might be counted more than once in overlapping sections, a correction factor (CF) was calculated and applied to the cell counts to compensate for this effect (Abercrombie, M., *Anat. Rec.* 94:239–247 (1946); Burstein et al., *Brain Res.* 511:329–337 (1990)). This CF was obtained from a measurement of the longitudinal diameter of X-Gal labelled neurons observed in sagittal sections of trigeminal ganglia obtained four days after inoculation with tkLTRZ1. Randomly chosen neurons (n=9) from these sections were examined under 100× magnification. Neuronal cell diameters were measured in the sagittal plane. The mean of these cell diameters and the section thickness were used to calculate the correction factor (Abercrombie, M., *Anat. Rec.* 94:239–247 (1946); Burstein et al., *Brain Res.* 511:329–337 (1990)); CF (correction factor) equals mean section (M) thickness divided by the mean section thickness plus the longitudinal diameter (LD) of the cell (CF=M/M+LD). The number of neurons present in a ganglion from any animal was estimated by multiplying the total number of neurons counted by the appropriate correction factor (calculated number of neurons=total neurons counted×CF).

Comparison between the number of neurons labeled with each vector and between the different time points after inoculation was performed using a one factor analysis of variance (SuperAnova, Abacus).

2. Results a. Histochemical Labelling with X-Gal Substrate

Figure 11:
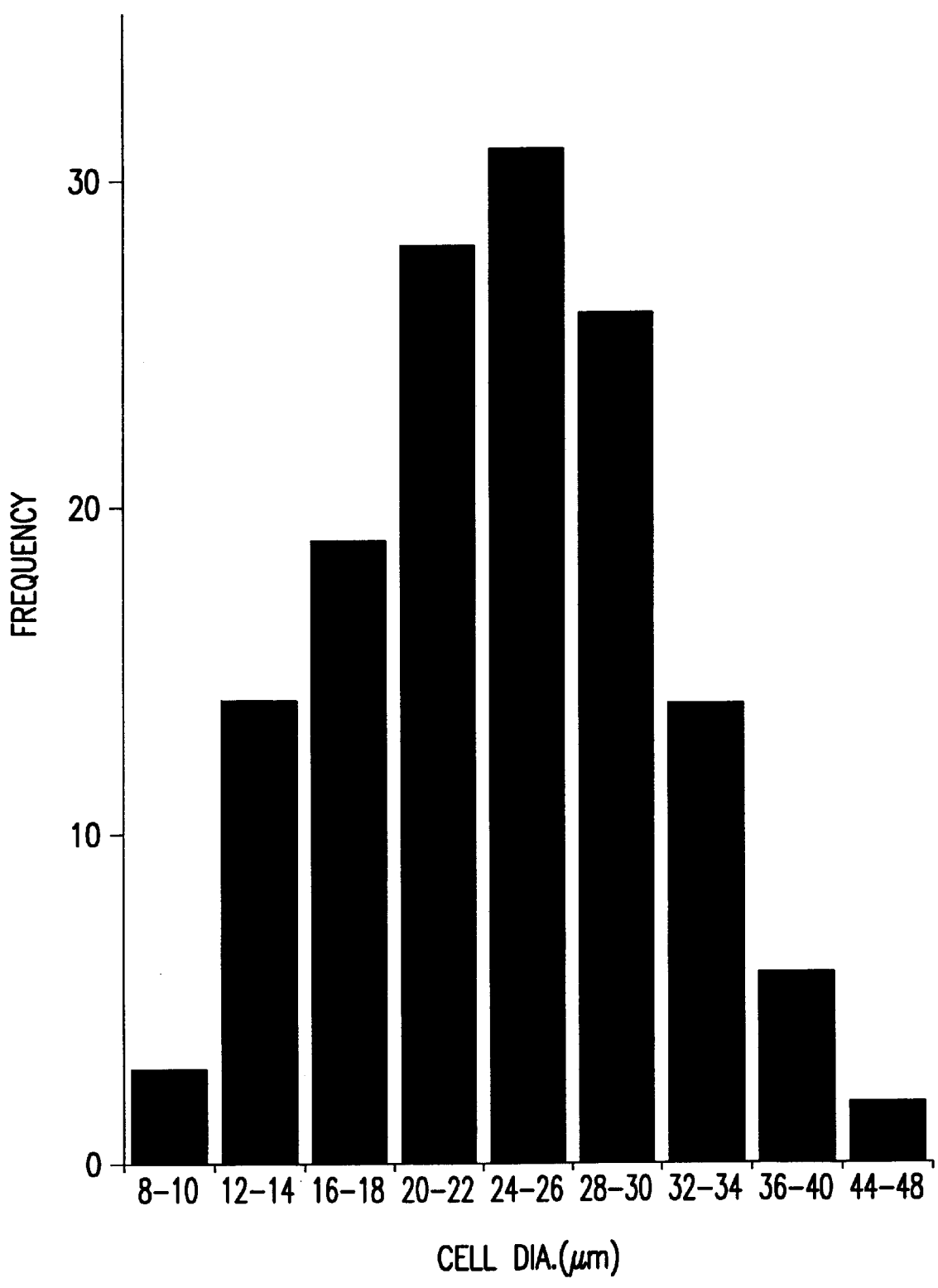
FIG. 11 illustrates a frequency histogram of the longitudinal diameters of X-Gal labeled. neurons in sagittal sections from the trigeminal ganglion of one animal obtained 4 days after inoculation with vector tkLTRZ1.

Light microscopy of histochemically-reacted coronal sections from the ipsilateral trigeminal ganglia of mice inoculated with lacZ-containing vectors (tkLTRZ1, RH116, and NSE-lacZ-TK) revealed labeled neurons of varying size. In one representative case examined 4d following inoculation with vector tkLTRZ1, labeled neurons ranging from 8–48 μm in longitudinal diameter, were observed, (FIG. 11). Labeling of non-neuronal cells was not observed in experimental animals at any time point tested. A benign infiltrate of cells with lymphocytic morphology, primarily localized to the border of ganglionic tissue was occasionally observed in tissue sections from some mice. No evidence of degeneration or death of neurons, or satellite cells (residual nodules of Naegotte) was observed.

Four neuronal staining patterns were observed: (1) a dense diffuse blue stain which filled the cytoplasm. This staining pattern was also observed within single and branching peripheral processes which at times clearly originated from labelled neurons; (2) A lighter, speckled, diffuse blue stain; (3) A granular, cytoplasmic, staining pattern with or without a densely labeled nucleus, and (4) A light, speckled, diffuse stain as above in the second pattern of staining, with granular cytoplasmic staining as well. The third staining pattern occurred most frequently. The first pattern was rarely seen at time points beyond 4d, and nuclei-labeling was rarely observed prior to 14d.

Figure 12:
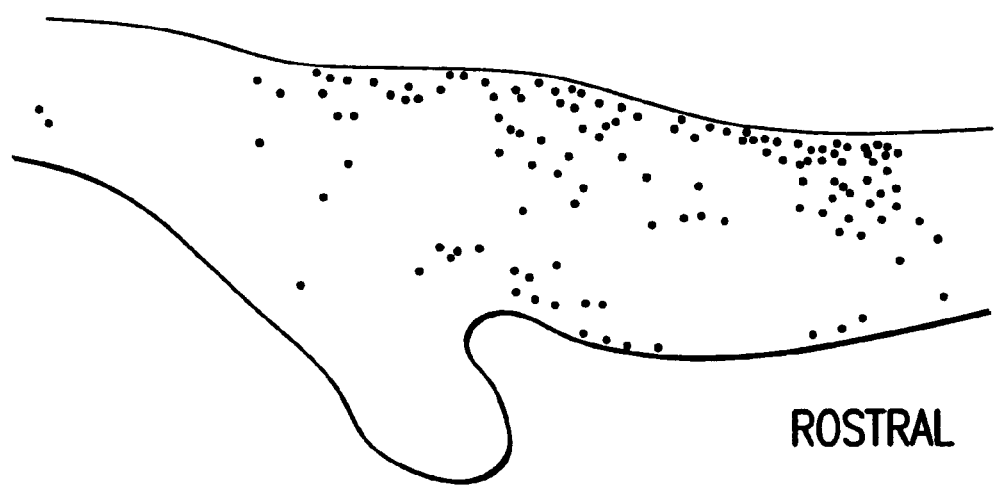
FIG. 12 illustrates the reconstruction of the distribution of X-Gal labeled neurons within sections from the trigeminal ganglion obtained 4 days after inoculation with vector tkLTRZ1. Labeled neurons are in a rostromedial and central distribution.

Within the trigeminal ganglion, labelled neurons were observed in a rostral distribution along the medial aspect and in the central region of the ganglion (FIG. 12). These regions of the trigeminal ganglion are represented primarily by neurons from the first and second divisions of the trigeminal nerve (Arvidson, B., *J. Neurocytol.* 8:751–764 (1979); Bigotte et al., *Neurol.* 37:985–992 (1987); Kuwayama et al., *Brain Res.* 405:220–226 (1987); Margolis et al., *Curr. Eye Res.* 6(1):119–126 (1987)).

When the trigeminal ganglion from the non-inoculated side was examined labelled neurons were only occasionally seen, possibly as a result of inadvertent inoculation of the contralateral snout by mice during normal face grooming behavior. When trigeminal ganglia from control mice were examined 4d after inoculation with vector dlsptk, or 4d after shaving and scarification alone, no labeled neurons were seen.

Figure 13:
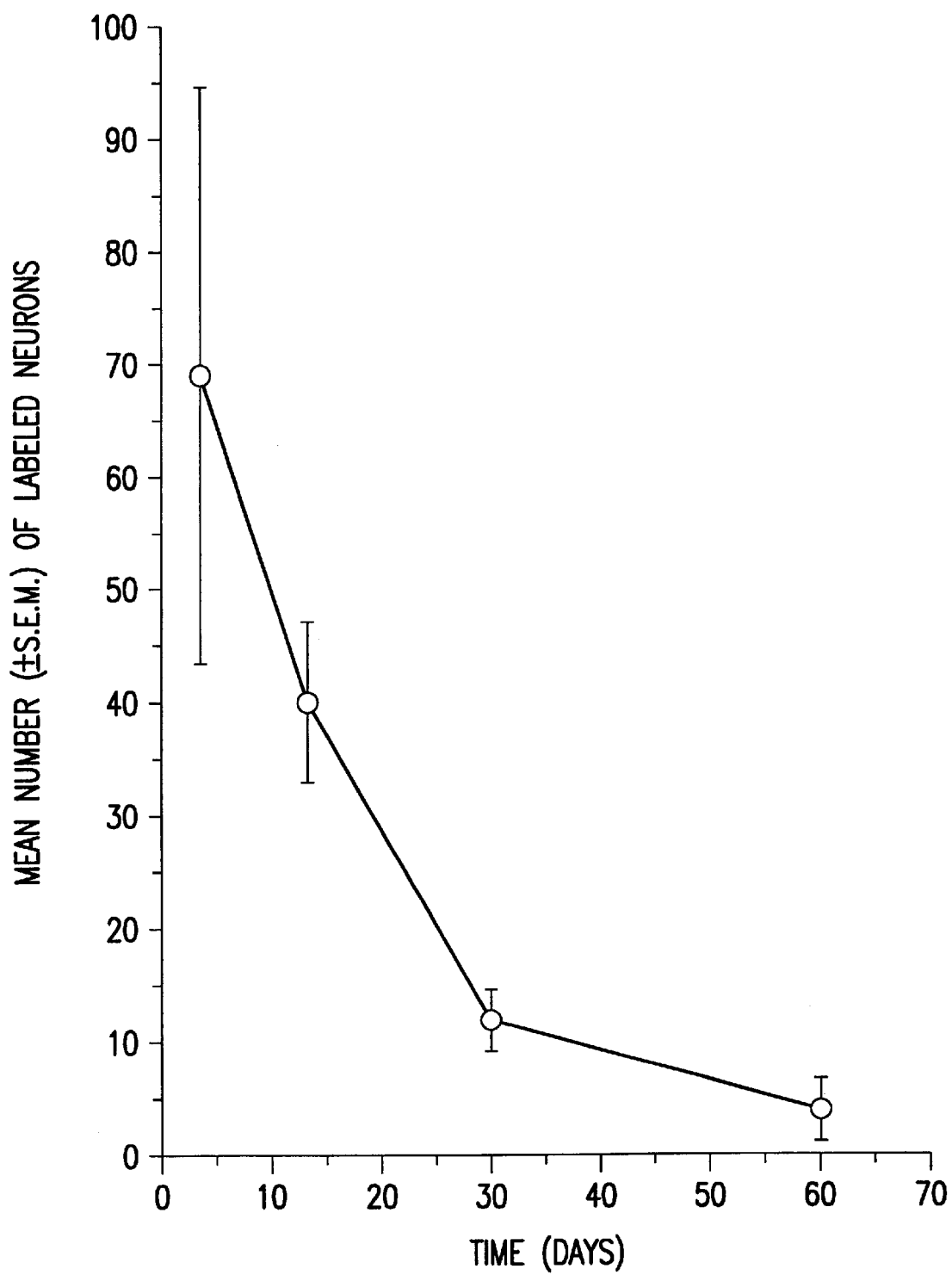
FIG. 13 illustrates a graph of the time course of X-Gal labeling of neurons with vector tkLTRZ1. The greatest mean number of labeled neurons was found at 4d post-inoculation.

Labeled neurons were counted and the correction factor for section thickness (see Methods) was applied to obtain an estimate of the total number of labeled neurons per ganglion. The mean number of labeled neurons for each vector at each time point is shown in Table 4. Inoculation with vector tkLTRZ1 produced a significantly greater mean number of labeled neurons at 4d than inoculation with vectors RH116 or NSE-lacZ-TK (F(2)=5.686, p=0.0136). Post-hoc comparison of means revealed that the mean number of neurons labeled with tkLTRZ1 was significantly greater than the mean number of neurons labeled with RH116 (p=0.0338) or NSE-lacZ-TK (p=0.0367) at this time point. There was no significant difference between the number of neurons labeled at 4d with vectors RH116 and NSE-lacZ-TK. Since labeled neurons were not observed with either RH116 or NSE-lacZ-TK at 14d after inoculation (Table 4), further evaluation was not done at 30 or 60d with these vectors. In contrast, with vector tkLTRZ1, neuronal labeling was observed at all time points but the number of labeled neurons showed a gradual and significant (F(3)=4.047, p=0.0204) decline with time (FIG. 13).

b. Beta-galactosidase-like Immunoreactivity

To confirm the presence and distribution of *E. coli* beta-galactosidase in the trigeminal ganglion after corneal and snout inoculation with lacZ-containing vectors, sections from additional mice inoculated with tkLTRZ1 were processed for immunocytochemistry. Neurons were labeled with polyclonal antibodies to *E. coli* β-galactosidase. Similar to the results with X-Gal histochemical staining, trigeminal ganglion neurons containing beta-galactosidase-like immunoreactivity were observed ipsilateral to the inoculation site. Labeled neurons were not observed in sections obtained from the trigeminal ganglion contralateral to the inoculation site in the animals examined here. The intracellular distribution of immunoreactivity resembled the first pattern of staining (dense cytoplasmic staining, see above pattern 1) seen in trigeminal ganglia reacted with X-Gal; diaminobenzibine reaction product completely filled the cytoplasm, partially or completely obscuring the nucleus.

c. LAT Transcripts in Trigeminal Ganglion

To compare the distribution of neurons expressing lacZ with the distribution of neurons harboring virus in the latent state, in situ hybridization to latency-associated transcripts was performed 6d after inoculation with vector NSE-lacZ-TK. Positive hybridization signal was observed over the nuclei of several trigeminal ganglion neurons ipsilateral to inoculation. Labeled neurons were found in a distribution within the ganglion similar to that observed for beta-galactosidase after inoculation with vector tkLTRZ1 and histochemical staining with X-Gal. Similar to the results with X-Gal staining, occasional LAT-positive neurons were observed in sections obtained from the contralateral ganglion.

d. Fluoro-Gold Labeling

The distribution of X-Gal labeled neurons after inoculation of tkLTRZ1, and LAT-positive neurons after inoculation of NSE-lacZ-tk, was also compared to the distribution of fluorescent labeled neurons after inoculation of the retrograde tracer Fluoro-Gold onto the cornea and snout. With this technique, large numbers of labeled neurons (greater than 25% of neurons from regions of the ganglia supplying the cornea and snout) were observed occupying the central and rostromedial regions of the trigeminal ganglion.

TABLE 4

Mean Number (± S.E.M.) of X-Gal Labeled Neurons in Trigeminal Ganglion After Corneal and Snout Inoculation of tkLTRZ1

|  | Days (d) post-inoculation | | | |
| --- | --- | --- | --- | --- |
|  | 4d | 14d | 30d | 60d |
| RH116 | 2 ± 1 (6) | 0 (8) | — | — |
| NSE-lacZ | 4 ± 2 (6) | 0 (6) | — | — |
| tkLTRZ1 | 69 ± 26 (7)+ | 40 ± 7 (7) | 12 ± 2 (6) | ++4 ± 3 (6) |

The number of animals in each group is indicated in parentheses.
+Comparison of groups shows a significant difference at 4d (ANOVA:p = 0.01).
++Comparison of time points shows significant difference for tkLTRZ1 (ANOVA: p = 0.02).

3. Discussion

In these experiments, retrogradely transported TK− herpes virus vectors were used to deliver the gene lacZ, to trigeminal ganglion neurons. Labeled neurons were of a size range comparable to that previously described for mouse trigeminal ganglion neurons and showed several different patterns of intracellular labelling for beta-galactosidase. The greatest number and longest duration of labelling was observed with a vector (tkLTRZ1) containing lacZ downstream of the Moloney murine leukemia virus long terminal repeat promoter (MoMLV-LTR). The distribution of X-Gal labelled neurons in trigeminal ganglion after inoculation of tkLTRZ1 was similar in location to neurons expressing latency-associated transcripts (LATs), and to neurons labeled with the retrograde tracer Fluoro-Gold. The significance of each, of these points is discussed below.

a. The Significance of the Different Patterns of Intracellular Labeling Observed in Neurons with X-Gal Histochemistry Although a variety of intracellular labeling patterns observed with X-Gal histochemistry, the predominant pattern was a granular cytoplasmic stain. This type of labeling has been suggested by Dobson et al., Neuron 5:353–360 (1990) to be due to the association of histochemical reaction product with membrane-bound organelles. Since this pattern of intracellular labeling is similar to the distribution of lysosomal and non-lysosomal acid hydrolases observed in mouse sensory ganglion (Sommer et al., Brain Res. 346:310–326 (1985)), granular cytoplasmic staining may represent histochemical reaction product that was being degraded by lysosomal or other cellular enzymes. Although the observed distribution of intracellular labelling could also have been the result of metabolism of X-Gal by endogenous lysosomal enzymes rather than by E. coli β-galactosidase (Zhang et al., The FASEB J. (5):3108–3113 (1991)), the inoculation of non-lacZ-containing virus (dlsptk) and scarification without inoculation, both of which might induce endogenous hydrolase activity, were not associated with neuronal labeling.

The other patterns of intracellular staining observed in these experiments may have reflected variable levels of expression of lacZ in trigeminal ganglion neurons. The presence of dense nuclear labelling in some neurons at 14d but not at 4d may have been the result of gradual accumulation and/or concentration of the histochemical reaction product within nuclei.

b. Vector tkLTRZ1 Produced the Largest Number of Labelled Neurons and the Longest Duration of Labeling The large number of neurons labeled and the presence of labeling for up to 6d with vector tkLTRZ1, was an effect of the MoMLV-LTR promoter (Price et al., Proc. Natl. Acad. Sci. USA 84:156–160 (1987); Dobson et al., Neuron 5:353–360 (1990)) used in this vector. The presence of this promoter, which should be constitutively active in all cell types, has been previously shown to be associated with long term stable expression of lacZ in sensory neurons in mice (Dobson et al., Neuron 5:353–360 (1990)).

In contrast to the results obtained with vector tkLTRZ1, inoculation with vector RH116, which contains an HSV delayed-early promoter (beta 8), resulted in small numbers of neurons being labeled at the earliest time point but not at subsequent time points. The short duration of labelling with this vector was an effect of the beta 8 promoter which is active during viral replication, and not during latency. Consistent with these results in the peripheral nervous system, Huang et al., Exp. Neurol. 115:303–316 (1992) and Andersen et al., Human Gene Therapy, (in press) (1992), have demonstrated only short term labeling of neurons after inoculation of vector RH116 into the central nervous system.

Similar to the results obtained with vector RH116, vector NSE-lacZ-TK, containing the neuron-specific enolase promoter (Forss-Petter et al., Neuron 5:187–197 (1990)), labeled small numbers of neurons at the earliest, but not subsequent time points. Although this enzyme is expressed in most neurons, different levels of NSE promoter activity have been described in the nervous system. Frontal cortex and hippocampus reportedly demonstrate higher levels of promoter activity (as determined by reporter gene expression) than other regions of the nervous system (Forss-Petter, unpublished observations). In addition, radioimmunoassay methods have demonstrated low levels of NSE in the peripheral nervous system when compared with the central nervous system (Marangos et al., Ann. Rev. of Neurosci., Palo Alto, Calif., Annual Reviews, Inc. pp. 269–297 (1987)). The small number and limited duration of neuronal labelling with the NSE promoter in the present experiments may therefore reflect weak activity of this promoter in peripheral sensory neurons.

Although weak promoter function may have contributed to the low level expression of lacZ in vectors RH116 and NSE-lacZ-TK, there may have been small amounts of *E. coli* β-galactosidase present that we could not detect with our histochemical methods.

c. Neuronal Labelling Seen with Vector tkLTRZ1 Decreased with Time

Although large numbers of labeled neurons were initially observed after inoculation with vector tkLTRZ1, the number of labeled neurons gradually decreased over time reaching lowest levels at 60d. This gradual decline in the number of labeled neurons may have been the result of a gradual loss of promoter function, as has been observed with the LTR promoter (Palmer et al., *Proc. Natl. Acad. Sci. USA* 88:1330–1334 (1991)) in some in vivo situations. In contrast with these results, Dobson et al., *Neuron* 5:353–360 (1990) described neuronal labeling for up to 24 weeks with a vector containing lacZ downstream of the MoMLV-LTR promoter inserted into the HSV immediate-early gene ICP4. Since the same promoter was used in the present experiments with vector tkLTRZ1, the observed gradual reduction in neuronal labeling may have been due to the location of this promoter within the TK gene. Inserting the LTR promoter at other sites within the HSV genome will therefore increase the stable expression of lacZ or other genes. Alternatively, the use of promoters known to be active in latency (e.g., the LAT promoter) (Margolis et al., *Virol.* 189:150–160 (1992)) might lead to stable expression of foreign genes. However, a gradual decrease in labeling has also been recently reported even with a vector containing lacZ downstream of the LAT promoter (Sawtell et al., *J. Virol.*:2157–2169 (1992)).

The gradual decrease in the number of labeled neurons after inoculation with vector tkLTRZ1 could possibly have been the result of degeneration or death of HSV-infected neurons in trigeminal ganglia. However, this TK– vector is known to be replication-defective in neurons, and its use in these experiments was not associated with signs of degeneration or death of trigeminal ganglion neurons at any time point after inoculation.

d. Variation in lacZ Expression with Different TK-HSV Vectors

The variation in expression of lacZ seen with vector tkLTRZ1, which was greatest at 4d after inoculation, may have reflected variability in the efficacy of the MoMLV-LTR promoter during the early stages of infection. Other factors that might have contributed to the variation in lacZ expression include: differences in technique (e.g., different depth of incisions produced by needle scarification), variation in the uptake of HSV by sensory terminals, or variation in the activity of the different viral and mammalian promoters within subtypes of trigeminal ganglion neurons. Similar variation in the number of labeled neurons has been previously described by Dobson et al., *Neuron* 5:353–360 (1990) in mouse dorsal root ganglia after sciatic nerve injection of a replication-defective, lacZ-containing HSV vector.

e. The Significance of the Distribution of Neurons Labeled with lacZ-containing TK-HSV Vectors Presently, rostromedial labeling of neurons in trigeminal ganglion was observed with X-Gal histochemistry and with in situ hybridization for LATs after corneal and snout inoculation with lacZ-containing TK– vectors. A similar distribution of neuronal labeling was observed after inoculation of the retrograde tracer Fluoro-Gold onto these same facial regions. This distribution is consistent with the results of experiments in which replication-competent HSV and the retrograde tracer wheat germ agglutinin (WGA-HRP) (Margolis et al., *Curr. Eye Res.* 6(1):119–126 (1987)), or horseradish peroxidase (HRP) (Arvidson, B., *J. Neurocytol.* 8:751–764 (1979)) were injected into the anterior chamber of the mouse eye. Degeneration of trigeminal ganglion cells in an anteromedial distribution was also observed by Bigotte et al., *Neurology* 37:985–992 (1987) after injection of the toxin doxorubicin into the mouse cheek. The similarity between the results of these retrograde tracing and degeneration studies, and the distribution of X-Gal, LATs, and Fluoro-Gold labeling in the present experiments, is evidence of the specific uptake and axonal transport of both TK-HSV and Fluoro-Gold by neurons supplying the ophthalmic and maxillary divisions of the trigeminal nerve. The large number of neurons labeled with Fluoro-Gold in comparison with vector inoculation and histochemistry with X-Gal is consistent with the known efficacy of this substrate as a retrograde axonal tracer (Burstein et al., *Brain Res.* 511:329–337 (1990)). The results obtained with the TK-HSV vectors used in these experiments is evidence that replication-defective HSV mutants can be used to deliver functional genes to trigeminal ganglion neurons in an anatomically predictable manner.

4. Conclusions

These data demonstrate the effectiveness of TK– (replication defective) herpes simplex viruses as vectors for the delivery of genes (for example, lacZ) to neurons, including sensory neurons of the trigeminal ganglion. A vector containing the gene lacZ downstream of the constitutive Moloney murine leukemia virus long terminal repeat promoter (tkLTRZ1) labeled the largest number of sensory neurons in trigeminal ganglion, and gave the longest duration of labeling of the vectors tested. Since the vectors used in these experiments labeled neurons within specific regions of the trigeminal ganglion, they are useful for the delivery of a desired gene, including functional genes, to anatomic subsets of sensory neurons. Such functional genes include, for example, toxic or killing genes which permit the development of experimental models of painful neuropathy (e.g., post herpetic neuralgia) or which alleviate pain. These vectors can also be used to deliver analgesic neuropeptides (e.g., the genes for the opioid peptides including for example dynorphin and enkephalin) to sensory neurons or CNS neurons to change the physiology of these neurons.

Example 5

The enkephalins are a class of endogenous opioid peptides thought to be involved in many physiological functions in the nervous system. In particular, many lines of evidence point to their role in the modulation of nociception.

To assess the actions of enkephalins both in vivo and in vitro, and to develop potential means to modulate nociception in vivo, a series of herpes simplex virus-1 (HSV-1) recombinants aimed at expressing the human proenkephalin gene in neural cells following infection, were derived. It has been previously shown that HSV-1 recombinant viruses can be used to confer long term expression of a foreign gene in postmitotic neurons (Dobson et al., *Neuron* 5:353–360 (1990)).

To construct the recombinant viruses, the human proenkephalin cDNA, under the control of various promoter elements, was inserted into the coding region of the viral thymidine kinase gene (TK) in a plasmid vector. These transcriptional units were then inserted into the viral genome by homologous recombination between plasmidial and viral DNA at the TK site. A mammalian promoter can be active when inserted in that region of the viral genome. Some of the proenkephalin constructs were fitted with a minimal human proenkephalin promoter coupled to one or multiple copies of a cAMP/pKC-inducible enhancer element. Alternatively, a proenkephalin construct bearing the Moloney murine leukemia virus LTR promoter/enhancer element was also constructed. Different HSV-1 viral genomes were selected for insertion of the proenkephalin transcription units within their TK gene: wild-type KOS virus, but also mutant viruses with compromised replication or reduced cytopathogenicity.

These vectors can be taken up from peripheral sites and transported to the nuclei of sensory neurons via retrograde transport. Based on previous work by ourselves (Davar et al. submitted) and others (e.g., Dobson et al., *J. Virol.* 63:3844–3851 (1989)) these vectors should be non-toxic and effect expression of the transgene. Since many of these neurons normally process peptide prohormones in vesicles and release these peptides at synaptic terminals in the spinal cord, they are able to co-release enkephalins. Based on studies of infusion of enkephalins into the spinal cord, these molecules should reduce the sensation of pain.

While the invention has been described in connection with the specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Modifications of the above-described modes for carrying out the invention that are obvious to persons of skill in medicine, immunology, neurology, physiology, virology, pharmacology, and/or related fields are intended to be within the scope of the following claims.

All publications and patent applications mentioned in this specification are indicative of the level of skill of those skilled in the art to which this invention pertains. All publications and patent applications are herein incorporated by reference, to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of expressing a gene sequence in a neuronal cell of the central nervous system, said method comprising:

directly administering into said neuronal cell a herpes simplex virus 1 (HSV-1) mutant as a vector for gene delivery, said HSV-1 mutant comprising:
   (a) a deletion in an immediate early gene whereby said deletion in an immediate early gene is replaced by
   (b) a gene sequence operably linked to a promoter sequence so that said gene sequence will be expressed in said neuronal cell, and expressing said gene sequence in said neuronal cell.

2. The method of claim 1, wherein said immediate early gene encodes infected cell proteins (ICPs) 0, 4, 22, 27, or 47.

3. The method of claim 1, wherein said gene sequence is a mammalian gene sequence that encodes an analgesic neuropeptide, a neurotransmitter, a neurotransmitter antagonist, a toxic protein or polypeptide, a protein that modulates neuronal physiology, or a protein that can be used to treat an individual with a neurological defect, deficiency, or unbalanced state.

4. The method of claim 1, wherein said promoter is a mammalian promoter.

5. The method of claim 4, wherein said mammalian promoter is neuronal specific enolase (NSE), neurofilament (NF), thy-1, tyrosine hydroxylase, or enkephalin.

6. The method of claim 1, wherein said HSV-1 mutant infects said neuronal cells without a helper virus.

7. The method of claim 2, wherein said immediate early gene encodes infected cell protein (ICP) 0.

8. The method of claim 2, wherein said immediate early gene encodes infected cell protein (ICP) 4.

9. The method of claim 2, wherein said immediate early gene encodes infected cell protein (ICP) 22.

10. The method of claim 2, wherein said immediate early gene encodes infected cell protein (ICP) 27.

11. The method of claim 2, wherein said immediate early gene encodes infected cell protein (ICP) 47.

12. The method of claim 1, wherein said promoter is the HSV promoter for the latency-associated transcript (LAT).

* * * * *

UNITED STATES PATENT AND TRADEMARK OFFICE
CERTIFICATE OF CORRECTION

PATENT NO.   : 6,610,287 B1
DATED        : August 26, 2003
INVENTOR(S)  : Breakefield et al.

It is certified that error appears in the above-identified patent and that said Letters Patent is hereby corrected as shown below:

<u>Title page,</u>
Item [56], References Cited, OTHER PUBLICATIONS, please add the following references:

-- Johnson, P.A. *et al.*, "Cytotoxicity of a Replication-Defective Mutant of Herpes Simplex Virus Type 1," *J. Virology 66*:2952-2965 (May 1992).
Johnson, P.A. *et al.*, "Effects of gene transfer into cultured CNS neurons with a replication-defective herpes simplex virus type 1 vector," *Mol. Brain Res. 12*:95-102 (January 1992).
Johnson, P.A. *et al.*, "Improved Cell Survival by the Reduction of Immediate-Early Gene Expression in Replication-Defective Mutants of Herpes Simplex Virus Type 1 but Not by Mutation of the Virion Host Shutoff Function," *J. Virology 68*:6347-6362 (October 1994).
Krisky, D.M. *et al.*, "Deletion of multiple immediate-early genes from herpes simplex virus reduces cytotoxicity and permits long-term gene expression in neurons," *Gene Therapy 5*:1593-1603 (1998).
Post, L.E. and B. Roizman, "A Generalized Technique for Deletion of Specific Genes in Large Genomes: α Gene 22 of Herpes simplex Virus 1 Is Not Essential for Growth," *Cell 25*:227-232 (1981).
Sacks, W.R. *et al.*, "Herpes Simplex Virus Type 1 ICP27 Is an Essential Regulatory Protein," *J. Virology 55*:796-805 (1985).
Samaniego, L.A. *et al.*, "Persistence and Expression of the Herpes Simplex Virus Genome in the Absence of Immediate-Early Proteins," *J. Virology 72*:3307-3320 (1998).

UNITED STATES PATENT AND TRADEMARK OFFICE
CERTIFICATE OF CORRECTION

PATENT NO.     : 6,610,287 B1
DATED          : August 26, 2003
INVENTOR(S)    : Breakefield et al.

It is certified that error appears in the above-identified patent and that said Letters Patent is hereby corrected as shown below:

OTHER PUBLICATIONS, cont'd,
Sears, A.E. *et al.*, "Herpes Simplex Virus 1 Mutant Deleted in the $\alpha 22$ Gene: Growth and Gene Expression in Permissive and Restrictive Cells and Establishment of Latency in Mice," *J. Virology 55*:338-346 (1985).
Wu, N. *et al.*, "Prolonged Gene Expression and Cell Survival after Infection by a Herpes Simplex Virus Mutant Defective in the Immediate-Early Genes Encoding ICP4, ICP27, and ICP22," *J. Virology 70*:6358-6369 (September 1996). --

Signed and Sealed this

Thirtieth Day of December, 2003

JAMES E. ROGAN
*Director of the United States Patent and Trademark Office*